US005635469A

United States Patent [19]

Fowler et al.

[11] Patent Number: 5,635,469

[45] Date of Patent: Jun. 3, 1997

[54] FOAMING CLEANSING PRODUCTS

[75] Inventors: Timothy J. Fowler, Cincinnati; Frederick W. Woodin, Jr., Middletown; George E. Deckner; Anil J. Gupte, both of Cincinnati, all of Ohio; Tatsuya Taniguchi, Hyogo, Japan; Dimitris I. Collias, Cincinnati, Ohio

[73] Assignee: The Procter & Gamble Company, Cincinnati, Ohio

[21] Appl. No.: 729,523

[22] Filed: Oct. 10, 1996

Related U.S. Application Data

[63] Continuation of Ser. No. 602,387, Feb. 16, 1996, abandoned, which is a continuation of Ser. No. 438,457, May 10, 1995, abandoned, which is a continuation of Ser. No. 75,210, Jun. 10, 1993, abandoned.

[51] Int. Cl.$^6$ .................................................. C11D 17/00
[52] U.S. Cl. ........................ 510/406; 239/329; 239/330; 239/343; 239/590; 239/590.3; 239/575; 510/120; 510/475
[58] Field of Search ................................. 239/329, 330, 239/343, 590, 590.3, 575; 510/120, 406, 475

[56] References Cited

U.S. PATENT DOCUMENTS

| | | | |
|---|---|---|---|
| 2,532,565 | 12/1950 | Miller | 259/4 |
| 2,624,622 | 1/1953 | Holte | 299/89 |
| 2,651,546 | 9/1953 | Palm | 299/107 |
| 2,715,045 | 8/1955 | Thompson | 299/86 |
| 3,388,868 | 6/1968 | Watson et al. | 239/427 |
| 3,709,437 | 1/1973 | Wright | 239/343 |
| 3,937,364 | 2/1976 | Wright | 222/190 |
| 3,962,150 | 6/1976 | Viola | 252/542 |
| 3,974,208 | 8/1976 | Dudzinski et al. | 260/501.11 |
| 4,022,351 | 5/1977 | Wright | 222/145 |
| 4,044,923 | 8/1977 | Gardner | 222/190 |
| 4,147,782 | 4/1979 | Klein et al. | 424/230 |
| 4,156,505 | 5/1979 | Bennett | 239/321 |
| 4,184,615 | 1/1980 | Wright | 222/190 |
| 4,219,159 | 8/1980 | Wesner | 239/343 |
| 4,311,618 | 1/1982 | Schafer-Burkhard | 252/542 |
| 4,350,298 | 9/1982 | Tada | 239/343 |
| 4,432,496 | 2/1984 | Ito | 239/327 |
| 4,509,661 | 4/1985 | Sugizaki et al. | 222/190 |
| 4,663,158 | 5/1987 | Wolfram et al. | 424/70 |
| 4,690,818 | 9/1987 | Puchalski et al. | 424/70 |
| 4,726,915 | 2/1988 | Verdicchio | 252/542 |
| 4,769,169 | 9/1988 | Fishlock-Lomax | 252/106 |
| 4,839,081 | 6/1989 | Church et al. | 252/108 |
| 4,879,107 | 11/1989 | Vanlerberghe et al. | 424/70 |
| 4,880,161 | 11/1989 | Wright | 239/330 |
| 4,891,150 | 1/1990 | Gross et al. | 252/142 |
| 4,932,567 | 6/1990 | Tanabe et al. | 222/190 |
| 4,954,332 | 9/1990 | Bissett et al. | 424/59 |
| 4,963,535 | 10/1990 | Sebag et al. | 514/54 |
| 5,011,681 | 4/1991 | Ciotti et al. | 424/81 |
| 5,037,006 | 8/1991 | Kock | 222/190 |
| 5,064,103 | 11/1991 | Bennett | 222/190 |
| 5,232,632 | 8/1993 | Woo et al. | 252/546 |
| 5,364,031 | 11/1994 | Taniguchi et al. | 239/330 |

FOREIGN PATENT DOCUMENTS

| | | |
|---|---|---|
| 961015 | 1/1975 | Canada . |
| 250181 | 12/1987 | European Pat. Off. . |
| 61-118164 | 6/1986 | Japan . |
| 3-7963 | 1/1991 | Japan . |
| WO93/00089 | 1/1993 | WIPO . |

OTHER PUBLICATIONS

Karam and Bellinger "Deformation and Breakup of Droplets in a Simple Shear Field" Ind. Engng. Chem. Fundam, 7 576–581 (1968) No Month Available.

Grace, "Dispersion Phenomena in High Viscosity Immiscible Fluid Systems and Application of Static Mixers as Dispersion Devices in Such Systems", Chem. Engng. Commun. 14, 225–277 (1982) No Month Available.

Harnby, Edwards, and Nienow, "Mixing in the Process Industries", Chapter 12, Static Mixers, 225–249, Chapter 15, Gas–Liquid Dispersion and Mixing, 322–323. (1992) No Month Available.

*Primary Examiner*—Glenn A. Caldarola
*Assistant Examiner*—Elizabeth D. Wood
*Attorney, Agent, or Firm*—Anthony D. Sabatelli; David K. Dabbiere

[57] ABSTRACT

The present invention relates to foam producing products useful for personal cleansing. These products comprise a foamable liquid composition and a foam-producing foam dispenser. These products provide a stable homogeneous foam and good lathering and cleansing characteristics. These products are very mild to the skin and are useful for moisturizing the skin and for delivering a wide variety of active ingredients to the skin.

35 Claims, 6 Drawing Sheets

FOAMING CLEANSING PRODUCTS

This is a continuation of application Ser. No. 08/602,387, filed on Feb. 16, 1996 and now abandoned, which is a continuation of application Ser. No. 08/438,457, filed on May 10, 1995 and now abandoned, which is a continuation of application Ser. No. 08/075,210, filed on Jun. 10, 1993 and now abandoned.

TECHNICAL FIELD

The present invention relates to a foaming cleansing product comprising a mild, conditioning, aqueous cleansing composition and a foam dispenser for containing and subsequently delivering the composition as an aerated foam.

BACKGROUND OF THE INVENTION

Foaming cosmetic compositions for personal cleansing and cosmetic purposes must satisfy a number of criteria including good cleansing power and foaming properties.

Ideal cosmetic cleansers should cleanse the skin or hair gently, without causing irritation, without dehydrating the skin, and without leaving the skin feeling taut after use. Ideal cosmetic cleansers should also condition the skin. Most lathering soaps, liquids, gels and bars fail in one or more of these respects.

For example, good foaming cleansers tend to be harsh to the skin. This occurs because the surfactant systems that provide good lathering performance, while being effective cleansers, also tend to dehydrate the skin and remove lipids from the skin. The skin becomes dry due to the hygroscopic effect of the surfactants, which remove water from the skin. The skin becomes tight, or taut due to the emulsification effects of the surfactants. The surfactants emulsify natural oils in the skin, which are then washed away when the cleansing composition is rinsed off.

Humectants are conditioning materials known in the skin care art for rehydrating skin and aiding in retention of water by the skin. Emollients are conditioning materials known in the art for remoisturizing the skin or hair with lipids or other oils or oily materials. However both of these types of conditioners are difficult to formulate into a lather-producing or foam-producing product. Mere addition of conventional conditioning agents, such as emollients and humectants, interfere with the lather forming ability of the surfactant. This is undesirable because consumers often associate foam and lather with cleansing ability, and tend to prefer foam or lather producing products for aesthetic reasons as well. Furthermore, the use of high-sudsing surfactants tends to be unduly harsh to the skin and occular tissue, even with the addition of conditioning ingredients. The use of milder surfactants can reduce adverse effects on the skin, but these surfactants generally have poor lather and foaming ability. The addition of skin conditioning components can further improve the skin mildness of these surfactants, but would further degrade foaming and lathering of an already poorly foaming and lathering composition.

Products that are highly effective for conditioning the skin are generally either non-cleansing or low-cleansing compositions, or if they cleanse, they do not provide high quality lather or foam. An example of this latter type of skin cleanser is an emollient cleanser. Emollient cleansers are typically creams which do not provide foam or lather.

Thus a need exists for cosmetic compositions which will produce a foam or lather which is abundant, stable and of high quality and compactness, which are effective cleansers, and yet which are very mild to the skin, hair and preferably occular mucosae, and further which can condition the skin. In particular, it is desirable to provide such a product which contains both emollients and humectants which are effective for remoisturizing and inhibiting dehydration of the skin.

One solution to this problem of achieving good foaming and cleansing characteristics without sacrificing mildness has been to deliver low foaming, mild surfactant compositions as a pre-foamed product. However, to do this requires that the delivery be made from an aerosol container employ propellant gasses. In light of heightened environmental and safety concerns, it would be highly desirable to achieve such foaming compositions without the use of aerosol containers and propellant gasses. However, current non-aerosol squeeze and pump foaming devices are unable to conveniently deliver foams having highly desired foaming and cleansing properties. These nonaerosol delivered foams tend to be thin and runny. Also, conventional non-aerosol foamers are not practicable for delivering compositions having a viscosity much above about 50 cps, unless inconveniently high actuation forces are used to dispense the product. In other words, consumers cannot conveniently dispense a viscous composition from a conventional non-aerosol foamer.

Further, known prior foam-producing, nonaerosol products still do not combine all the essential properties of an ideal product—i.e., good foam or lathering properties; effective cleansing; mildness; and conditioning, including both effective delivery of emollients and humectants; and delivery of a high quality foam from a non-areosol dispenser that is convenient for personal use. It is therefore an object of this invention to provide such a product.

In order to provide high quality lather or foam, conventional skin cleansing products based on surfactant cleansers typically contain from greater than 10% to about 20% of surfactants, typically including relatively high levels of anionic surfactants. Lather is produced as a result of physical agitation, e.g. rubbing with ones hands or mechanical devises (e.g., sponges and washcloths), on the skin. The high levels of surfactants used in these products have substantial dehydration and delipidization effects on the skin. Even products that contain humectants and emollients to compensate for this typically are not completely effective at restoring the skin to its original condition. It would be desirable to provide a foaming cleansing product which could restore the skin to its original levels of hydration and lipids. It is an additional object of this invention to provide such a product.

It would be further desirable to provide a foaming cleansing product which could provide effective cleansing and high quality foam and which could increase the level of hydration and/or lipid content at the skin surface upon use. It is yet another object of this invention to provide such a product.

These and other objects will become readily apparent from the detailed description which follows.

SUMMARY OF THE INVENTION

The present invention relates to a foam producing cleansing product comprising:

(A) a foamable cleansing liquid composition comprising
  (i) from about 0.1% to about 20% of a surfactant selected from the group consisting of amphoteric surfactants, nonionic surfactants, and mixtures thereof,
  (ii) from about 0.1% to about 10% of a water soluble cationic or nonionic polymer, (iii) from about 0.1% to about 25% of a humectant, (iv) from about 0.05% to about 10% of an emollient, and (v) from about 35% to about 99.65% water, wherein said liquid composition has a viscosity of from about 1 cps to about 300 cps; and (B) a foam dispenser for dispensing a final foam from an incoming intermediate foam, said dispenser comprising a reservoir to contain said liquid composition, a manually-actuatable means for generating a volume of a mixture of said liquid composition and a gas, and a foam dispensing nozzle sealably attached in fluid communication with said manually-actuatable means wherein the improvement comprises a nozzle comprising:

(i) an inlet conduit for receiving an intermediate foam consisting of a mixture of a liquid composition and a gas at a volumetric flow rate sufficiently high that it will produce an average incoming intermediate foam velocity which is too great to permit effective bubble bursting to put said foam in a final foam as said foam passes through at least one downstream foam refining means having a plurality of passageways therethrough; and (ii) a velocity decreasing means placing said inlet conduit in fluid communication with a foam refining means, wherein said velocity decreasing means lowers the average velocity of said intermediate foam so when said foam passes through said foam refining means it is at a velocity no greater than about 300 cm/sec.

In further embodiments, the present invention also relates to a foam producing cleansing product comprising:

(A) a foamable cleansing liquid composition comprising (i) from about 0.1% to about 20% of a surfactant selected from the group consisting of amphoteric surfactants, nonionic surfactants, and mixtures thereof, (ii) from about 0.1% to about 10% of a water soluble cationic or nonionic polymer, (iii) from about 0.1% to about 25% of a humectant, (iv) from about 0.05% to about 10% of an emollient, and (v) from about 35% to about 99.65% water, wherein said liquid composition has a viscosity of from about 1 cps to about 300 cps; and (B) a manually-actuable foam dispenser for producing and dispensing a high quality final foam from a foamable liquid and a gas, said foam being comprised of bubbles having a number-average diameter of about $D_1$, said dispenser comprising:

(i) a manually-actuable means for mixing a quantity of said foamable liquid with a quantity of said gas to produce an intermediate foam which comprises bubbles having a number-average diameter greater than about $D_1$ and a wider bubble size distribution than the final foam, at a volumetric flow rate Q which is dependent upon the speed of actuation of said manually-actuable means by the user; and (ii) a foam dispensing nozzle comprising a conduit in fluid communication with said manually-actuable means for receiving the intermediate foam from said manually-actuable means; and at least one foam refining means located in said conduit, said foam refining means comprising a plurality of substantially uniformly-sized and evenly distributed passageways; wherein said intermediate foam passes through said passageways at a velocity, $V_2$, falling within the range of a minimum velocity, $V_{2,min}$, and a maximum velocity, $V_{2,max}$, wherein the conditions needed to cause bursting of said bubbles having a diameter larger than about $D_1$ are met.

In even further embodiments, this invention is also useful for delivering a wide variety of additional active ingredients to the skin.

All percentages and ratios used herein are by weight or by a solids weights basis of the total composition and all measurements made are at 25° C., unless otherwise designated. The invention hereof can comprise, consist of, or consist essentially of, the essential as well as optional ingredients and components described herein.

DETAILED DESCRIPTION OF THE INVENTION

The foam producing cleansing products of the present invention comprise a foamable cleansing composition and a compressible nonaerosol dispenser. The invention can comprise a kit which contains the cleansing composition and the dispenser. The invention can also comprise a finished product of the cleansing composition disposed within or otherwise contained by the dispenser.

By the term "foam producing cleansing product" as used herein is meant a product that produces or dispenses a foam (i.e. an aerated mixture of a liquid and air having a density less than the non-aerated liquid) which is useful for personal cleansing purposes. By the term "foamable cleansing liquid composition" as used herein is meant an aqueous based composition which is useful for personal cleansing and which is deliverable as a foam (i.e. which can be aerated) upon delivery from a nonaerosol dispensing device.

FOAMABLE CLEANSING COMPOSITION

The foamable cleansing compositions of the foam producing cleansing products of the present invention comprise the follow essential and optional components.

Surfactants

The compositions of the present invention comprise from about 0.1% to about 20%, more preferably from about 0.5% to about 15%, even more preferably from about 1% to about 10%, yet even more preferably from about 2% to about 8%, and most preferably from about 4% to about 8%, of a surfactant selected from the group consisting of amphoteric surfactants, nonionic surfactants, and mixtures thereof. The compositions containing up to about 10%, preferably up to about 8%, of the surfactant are especially desirable for use herein in that the products can provide high quality foam with a relatively low surfactant level. This is beneficial in that reduced surfactant levels provide reduced hygroscopic and delipidization effects on the skin, thereby reducing the rehydration and lipidization requirements (i.e. conditioning requirements) of the humectant and emollient needed to return the skin near to or at its original condition, or even to improve the skin from its pre-cleansing state.

A wide variety amphoteric and nonionic surfactants are useful herein and are disclosed in U.S. Pat. No. 5,151,209, to McCall et al., issued Sep. 29, 1992; U.S. Pat. No. 5,151,210, to Steuri et at., issued Sep. 29, 1992; and U.S. Pat. No. 5,120,532, to Wells et at., issued Jun. 9, 1992, all of which are incorporated by reference herein in their entirety. Without being limited by theory these nonionic and amphoteric surfactants are believed to provide the desired lathering and cleansing benefit while minimally interfering or inhibiting the other essential and optional components of the invention. The aforementioned lathering benefit of the type contemplated herein, of course, is achieved in conjunction with use of the later-described nonaerosol dispenser.

Among the nonionic surfactants that are especially useful herein are those that can be broadly defined as condensation products of long chain alcohols, e.g. C8–30 alcohols, with sugar or starch polymers, i.e., glycosides. These compounds can be represented by the formula $(S)_n$-O-R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel).

Other useful nonionic surfactants include the condensation products of alkylene oxides with fatty acids (i.e. alkylene oxide esters of fatty acids). These materials have the general formula $RCO(X)_n OH$ wherein R is a C10–30 alkyl group, X is -OCH$_2$CH$_2$- (i.e. derived from ethylene glycol or oxide) or -OCH$_2$CHCH$_3$- (i.e. derived from propylene glycol or oxide), and n is an integer from about 1 to about 100. Other nonionic surfactants are the condensation products of alkylene oxides with 2 moles of fatty acids (i.e. alkylene oxide diesters of fatty acids). These materials have the general formula $RCO(X)_n OOCR$ wherein R is a C10–30 alkyl group, X is -OCH$_2$CH$_2$- (i.e. derived from ethylene glycol or oxide) or -OCH$_2$CHCH$_3$- (i.e. derived from propylene glycol or oxide), and n is an integer from about 1 to about 100. Other nonionic surfactants are the condensation products of alkylene oxides with fatty alcohols (i.e. alkylene oxide ethers of fatty alcohols). These materials have the general formula $R(X)_n OR'$ wherein R is a C10–30 alkyl group, X is -OCH$_2$CH$_2$- (i.e. derived from ethylene glycol or oxide) or -OCH$_2$CHCH$_3$- (i.e. derived from propylene glycol or oxide), and n is an integer from about 1 to about 100 and R' is H or a C10–30 alkyl group. Still other nonionic surfactants are the condensation products of alkylene oxides with both fatty acids and fatty alcohols [i.e. wherein the polyalkylene oxide portion is esterified on one end with a fatty acid and etherified (i.e. connected via an ether linkage) on the other end with a fatty alcohol]. These materials have the general formula $RCO(X)_n OR'$ wherein R and R' are C10–30 alkyl groups, X is -OCH$_2$CH$_2$ (i.e. derived from ethylene glycol or oxide) or -OCH$_2$CHCH$_3$- (derived from propylene glycol or oxide), and n is an integer from about 1 to about 100. Nonlimiting examples of these alkylene oxide derived nonionic surfactants include ceteth-1, ceteth-2, ceteth-6, ceteth-10, ceteth-12, ceteraeth-2, cetareth-6, ceteareth-10, ceteareth-12, steareth-1, steareth-2, steareth-6, steareth-10, steareth-12, PEG-2 stearate, PEG-4 stearate, PEG-6 stearate, PEG-10 stearate, PEG-12 stearate, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{15}$ alkyl or alkenyl, more preferably $C_9$–$C_{17}$ alkyl or alkenyl, most preferably $C_{11}$–$C_{15}$ alkyl or alkenyl; and Z is a polyhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisitng of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$- moiety is derived from coconut oil fatty acids). Processes for making compositions containing polyhydroxy fatty acid amides are disclosed, for example, in G.B. Patent Specification 809, 060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$–$C_{18}$) and one contains an anionic water solubilizing group, e.g., carboxy, sulfonate, sulfate, phosphate, or phosphonate. Examples of amphoteric compounds are alkyl imino acetates, and iminodialkanoates and aminoalkanoates of the formulas $RN[CH_2)_m CO_2 M]_2$ and $RNH(CH_2)_m CO_2 M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivates, such as those of the formulas:

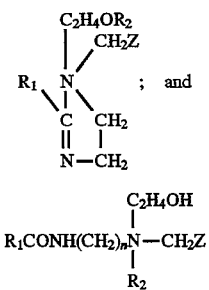

wherein $R_1$ is $C_8$–$C_{22}$ alkyl or alkenyl, $R_2$ is H, $CO_2 M$, $CH_2 CO_2 M$, or $CH_2 CH_2 M$, each Z is independently $CO_2 M$ or $CH_2 CO_2 M$, or $CH_2 CH_2 M$, and M is H, alkali or alkaline earth metal, ammonium, or alkonolammonium, and n is 1 to 4, preferable 2 to 3. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438, 091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Especially useful herein as amphoteric surfactants are the betaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other highly useful amphoterics include the sultaines and hydroxysultaines such as cocamidopropyl hydroxysultaine (available as Mirataine CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Among the nonionic and amphoteric surfactants useful herein preferred are those selected from the group consisting of lauryl polyglucoside, decyl polyglucoside, coconut alkyl N-methyl glucose amide, oleyl betaine, cocamidopropyl betaine, cocamidopropyl hydroxysultaine, sodium lauryl sarcosinate, coamdiopropyl PG-dimonium chloride phosphate, ceteth-2, ceteth-6, steareth-2, steareth-6, PEG-2 stearate, PPG-10 glyceryl stearate, and mixtures thereof. More preferred are those selected from the group consisting of lauryl polyglucoside, decyl polyglucoside, oleyl betaine, cocamidopropyl betaine, cocamidopropyl hydroxysultaine, sodium lauryl sarcosinate, coamdiopropyl PG-dimonium chloride phosphate and mixtures thereof.

Water Soluble Cationic or Nonionic Polymer

The foamable cleansing compositions comprise from about 0.1% to about 10%, preferably from about 0.5% to about 7.5%, and most preferably from about 1% to about 5% of at least one water-soluble cationic or nonionic polymer. By "water soluble" as used herein is meant that these polymers preferably have a solubility in distilled water at 25° C. of greater than 0.1 gm per 100 mL, more preferably greater than about 0.5 gm per 100 mL, most preferably greater than about 1 gm per 100 mL.

Without being limited by theory, it is believed that these polymers aid in depositing the humectants, emollients, and other active components of the cleansing compositions to the surface to be cleansed. The cationic polymers are believed to be especially useful because of their ability to associate with the negatively charged skin surface, thereby helping to keep the various components of the formulation upon the surface of the skin.

The nonionic and cationic polymers useful herein include those derived from both natural sources and synthetic sources. Among the polymers derived from natural sources, those that are derived from cellulose and proteins are highly preferred. Among the synthetic polymers, those that are polyethylenimines and polyacrylamides are preferred. The following are nonlimiting examples of cationic and nonionic polymers for use herein.

Cellulose derived polymers: By cellulose derived polymers as used herein is meant those containing a cellulose backbone, i.e. a polysaccharide backbone of repeating glucose units. In these cellulose derived polymers, the hydroxy groups of the cellulose polymer have been hydroxyalkylated (preferably hydroxyethylated or hydroxypropylated) to form a hydroxyalkylated cellulose which is then further modified with a cationic quaternary ammonium or protonated ammonium group. Preferred cationic modifying groups are those having at least one C10–20 alkyl chain and two shorter alkyl chains (i.e. C1 or C2) on the nitrogen. The substituent on the cellulose polymer can thus be depicted as $-(X)NRR'R''$ wherein X is hydroxyalkyl (preferably-$OCH_2CH_2$- or -$OCH_2CHOHCH_2$-), R and R' are methyl or ethyl, and R" is C10–20 alkyl [preferably lauryl, stearyl, or cocoyl (i.e. a mixture of alkyl groups derived from coconut oil)]. In other alternative structures it has been found that when R, R', and R" are all methyl (i.e. the trimonium group) that useful cellulose polymers are also obtained. In yet other alternative structures the cationic substituent on the cellulose contains both a hydroxyethyl and a hydroxypropyl group such that the moiety can be depicted as $-(OCH_2CH_2O)-CH_2CHOHCH_2NRR'R''$ wherein R, R', and R" are methyl or ethyl, and R" is C10–20 alkyl [preferably lauryl, stearyl, or cocoyl (i.e. a mixture of alkyl groups derived from coconut oil)], or alternatively wherein R, R', and R" are all methyl (i.e. the trimonium group).

Commercially avaialable cationic modified celluloses include: laurdimonium hydroxethyl cellulose (wherein in the above formula X is -$OCH_2CH_2$-, R and R' are methyl, and R" is lauryl), steardimonium hydroxyethyl cellulose (wherein in the above formula X is -$OCH_2CH_2$-, R and R' are methyl, and R" is stearyl), and cocodimonium hydroxyethyl cellulose (wherein in the above formula X is -$OCH_2CH_2$-, R and R' are methyl, and R" is cocoyl). These three materials are known by the trade names Crodacel QL, Crodacel QS, and Crodacel QM, respectively, which are all commercially available from Croda Corp. Another highly useful cationic cellulose is laurdimmonium hydroxypropyl oxyethyl cellulose (wherein the modifying group on the cellulose is $-(OCH_2CH_2O)-CH_2CHOHCH_2NRR'R''$, wherein R R' are methyl and R" is lauryl), which is commercially available as Crodacel QL Special, from Croda Corp.

Related to these cellulose polymers are ones having backbones that are derived from other sugars (or their related acids, alcohols, amines, etc.), e.g. galactose, mannose, arabinose, xylose, fucose, fructose, glucosamine, galactosamine, glucuronic acid, galacturonic acid, 5 or 6 membered ring polyalcohols, and mixtures thereof.

Protein derived polymers: The protein derived polymers useful herein are derived from a wide variety of protein sources. However, those that are derived from hydrolyzed proteins (i.e. proteins which are broken down into lower molecular weight segments of from about 1000 MW to about 5000 MW) are preferred. Hydrolyzed proteins are well known to the cosmetic chemist of ordinary skill in the art and can be derived using standard synthetic techniques such as the acid, alkaline, or enzymatic hydrolysis of various protein sources. The protein source used will determine the ultimate amino acid composition of the hydrolzyed protein obtained. Nonlimiting examples of hydrolyzed proteins which are useful as polymers herein include those selected from the group consisting of hydrolyzed casein, hydrolyzed collagen, hydrolyzed conchiorin protein, hydrolyzed corn protein, hydrolyzed elastin, hydrolyzed fibronectin, hydrolyzed hair keratin, hydrolyzed human placental protein, hydrozlyed keratin, hydrolyzed potato protein, hydrolyzed rice protein, hydrolyzed silk, hydrolyzed soy protein, hydrolyzed vegetable protein, hydrolyzed wool protein, hydrolyzed wheat protein, and mixtures thereof. These hydrolyzed proteins are described in the *CTFA International Cosmetic Ingredient Dictionary*, 1991, pp. 246–249, which are incorporated by reference herein in their entirety.

It has been found that cationically modified hydrolyzed proteins are especially useful polymers in the present invention. Using a variety of synthetic techniques known to the artisan of ordinary skill in the chemical arts, the nitrogen atoms of the amino acids comprising these hydrolyzed proteins can be hydroxyalkylated (preferably hydroxyethylated or hydroxypropylated) to form a hydroxyalkylated protein hydrolyzate which is then further modified with a cationic quaternary ammonium or protonated ammonium group. Preferred cationic modifying groups are those having at least one C10–20 alkyl chain and two shorter alkyl chains (i.e. C1 or C2) on the nitrogen. The substituent on the hydrolyzed protein can be depicted as -(X)NRR'R" wherein X is hydroxyalkyl (preferably-$OCH_2CH_2$- or-$OCH_2CHOHCH_2$-), R and R' are methyl or ethyl, and R" is C10–20 alkyl [(preferably lauryl, stearyl, or cocoyl (i.e. a mixture of alkyl groups derived from coconut fats)]. In other alternative structures it has been found that when R, R', and R" are all methyl (i.e. the trimonium group) that useful cationic hydrolyzed proteins are also obtained. Commercially avaialable cationic modified protein hydrolyzates include: hydroxypropyltrimonium hydrolyzed casein, hydroxypropyltrimonium hydrozlyed collagen, hydoxypropyltrimonium hydrolyzed keratin, hydroxypropyltrimonium hydrolyzed silk, hydroxypropyl trimonium hydrolyzed soy protein, hydroxypropyl trimonium hydrolyzed vegetable protein, and hydroxypropyltrimonium hydroylzed wheat protein, wherein the -(X)NRR'R" substituent on each of these protein hydrolyzates is such that X is -$OCH_2CHOHCH_2$-, and R, R', and R" are methyl. These hydrolyzed proteins are described in the *CTFA International Cosmetic Ingredient Dictionary*, 1991, pp. 254–255, which are incorporated by reference herein in their entirety. Other commercially avaialable cationic modified protein hydrolyzates include lauryldimonium hydroxypropyl hydrolyzed collagen, lauryldimonium hydroxypropyl hydrolyzed keratin,, lauryldimonium hydroxypropyl hydrolyzed silk, lauryldimonium hydroxypropyl hydrolyzed soy protein, stearyldimonium hydroxypropyl hydrolyzed casein, stearyldimonium hydroxypropyl hydrolyzed collagen, stearyldimonium hydroxypropyl hydrolyzed keratin, stearyldimonium hydroxypropyl hydrolyzed rice protein, stearyldimonium hydorxypropyl hydrolyzed silk, stearyldimonium hydroxypropyl hydrolyzed vegetable protein, stearyldimonium hydroxypropyl hydrolyzed wheat protein, cocodimonium hydroxypropyl hydrolyzed casein, cocodimonium hydroxypropyl hydrolyzed collagen, cocodimonium hydroxypropyl hydrolyzed keratin, cocodimonium hydroxypropyl hydrolyzed rice protein, cocodimonium hydroxypropyl hydrolyzed silk, cocodimonium hydroxypropyl hydrolyzed soy protein, cocodimnoium hydroxypropyl hydrolyzed wheat protein, wherein in each of these protein hydrolyzates the -(X)NRR'R" substituent is such that X is -$OCH_2CHOHCH_2$-, R and R' are methyl, and R" is lauryl or stearyl or cocoyl. These hydrolyzed proteins are described in the *CTFA International Cosmetic Ingredient Dictionary*, 1991, pp. 112–113, 293–294, 586, which are incorporated by reference herein in their entirety. Preferred among these cationic hydrolyzed proteins are lauryldimmonium hydroxypropyl hydrolyzed collagen, lauryldimmonium hydroxypropyl hydrolyzed kderatin, lauryldimmonium hydroxypropyl hydrolyzed keratin, lauryldimmonium hydroxypropyl hydrolyzed silk, lauryldimmonium hydroxypropyl hydrolyzed soy protein, and mixtures thereof.

Other water soluble polymers: Other useful water soluble polymers include polyvinylpyrrolidone and copolymers of vinylpyrrolidone such as those containing vinyl acetate, dimethylaminoethylmethacrylate and quaternary versions of the same with methyl sulfates, and polymers and copolymers of vinyl alcohol and vinyl acetate. Another highly useful polymer is the protonated form of polyethyleneimine. Polyethylenimine is a polymer which is produced from the polymerization of ethylenimine. The protonated polyethylenimine polymers preferred herein are those having a molecular weight of from about 500,000 to about 750,000, branching such that the ratio of primary to secondary to tertiary nitrogen is about 1:2:1, a tertiary nitrogen site on average at about every 3 to about 3.5 atoms, a charge density of about 20 mili-equizalvents per gram at pH 4.5, a density of about 1070 kg/m$^3$, and a viscosity of about 17,000 to about 28,000 milli-Pascals. A protonated polyethylenimine polymer meeting this description is commercially avaialable as Polymin P from BASF Corp.

Among the cationic polymers useful herein, preferred are those selected from the group consisting of lauryldimmonium hydroxypropyl oxyethyl cellulose, laurdimonium hydroxyethyl cellulose, steardimonium hydroxyethyl cellullose, cocodimonium hydroxyethyl cellulose, hydroxypropyl hydrolyzed collagen, lauryldimmonium hydroxypropyl hydrolyzed keratin, lauryldimmonium hydroxypropyl hydrolyzed keratin, lauryldimmonium hydroxypropyl hydrolyzed silk, lauryldimmonium hydroxypropyl hydrolyzed soy protein, protonated polyethylenimine, and mixtures thereof. More preferred are lauryldimonium hydroxypropyl hydrolyzed collagen, laurdimonium hydroxypropyl oxyethyl cellulose, and mixtures thereof.

Among the nonionic polymers useful herein, preferred are those selected from the group consisting of hydrolyzed casein, hydrolyzed collagen, hydrolyzed vegetable protein, polyvinylpyrrolidone, and mixtures thereof. More preferred is hydrolyzed casein.

Humectants

Another component of the compositions of the present invention is a humectant. When used herein, the humectant can comprise from about 0.1% to about 25%, more preferably from about 0.5% to about 15%, and most preferably from about 1% to about 10% of the compositions. As used herein, "humectant" means ingredients suitable for application to the hair or skin which promotes retention of water by the hair or skin. The humectants for use herein will be water soluble. By "water soluble" as used herein is meant that these polymers preferably have a solubility in distilled water at 25° C. of greater than 0.1 gm per 100 mL, more preferably greater than about 0.5 gm per 100 mL, most preferably greater than about 1 gm per 100 mL. Even though these materials are defined herein as humectants, they can also possess emolliency or moisturizing, or other conditioning or other properties.

Humectants are well known in the art of skin care and conditioning. Examples of humectants useful herein include materials such as urea; guanidine; glycolic acid and glycolate salts (e.g. ammonium and quaternary alkyl ammonium); lactic acid and lactate salts (e.g. sodium, ammonium, and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol, and the like; polyethylene glycol;

pyrrolidone carboxylic acids and their salts (e.g., sodium pyrrolidone carboxylic acid); sugars and starches; sugars and starches and their derivatives (e.g., honey extract, alkoxylated glucose); 6-(N-acetylamino)-4-oxahexyltrimonium chloride; hyaluronic acid; chitin, starch-grafted sodium polyacrylates such as Sanwet (RTM) IM-1000, IM-1500, and IM-2500 (available from Celanese Superabsorbent Materials, Portsmouth, Va.); lactamide monoethanolamine; acetamide monoethanolamine; propoxylated glycerol (as described in U.S. Pat. No. 4,976,953 to Orr et al., issued Dec. 11, 1990, which is incorporated by reference herein in its entirety); and mixtures thereof.

Preferred humectants useful in the compositions of the present invention are the C3–C6 diols and triols. More preferred as humectants are the C3–C6 diols and triols selected from the group consisting of propylene glycol, 1,3-dihydroxypropane, glycerin, urea; honey extract, butylene glycol, hexylene glycol, 1,4-dihydroxyhexane, 1,2,6-hexanetriol, and mixtures thereof. Most preferred as humectants are those selected from the group consisting of glycerin, urea, honey extract, butylene glycol, hexylene glycol, and mixtures thereof.

Emollients

The compositions of the present invention further comprise from about 0.05% to about 10%, preferably from about 0.075% to about 5%, and most preferably from about 0.10% to about 2% of an emollient. Exact levels of emollient will depend upon the material chosen with consideration being given to the effects upon lathering and foaming of the composition. Emollients in skin and personal care are materials which are used to replace or add to lipids and natural oils in the skin or hair. The term emollient, as used herein is intended to include conventional lipid materials (e.g., fats, waxes, and other water insoluble materials), polar lipids (e.g., lipid materials which have been hydrophylically modified to render them more water soluble), silicones, and hydrocarbons. The emollients for use herein are water insoluble. By "water insoluble" is meant materials which are not soluble as previously defined. In other words, by "water insoluble" is meant materials having a solubility in distilled water at 25° C. of less than about 1 gm per 100 mL, more preferable less than about 0.5 gm per 100 mL, and most preferably less than about 0.1 gm per 100 mL.

Without being limited by theory it is believed that these emollient materials help to provide a skin conditioning benefit by depositing upon the skin or hair during the cleansing and rinsing processes.

A wide variety of emollient materials are suitable for use in the compositions of the present invention.

Examples of conventional emollients include C8–30 alkyl esters of C8–30 carboxylic acids; C1–6 diol monoesters and diesters of C8–30 carboxylic acids; monoglycerides, diglycerides, and triglycerides of C8–30 carboxylic acids, cholesterol esters of C8–30 carboxylic acids, cholesterol, and hydrocarbons. Examples of these materials include diisopropyl adipate, isopropyl myristate, isopropyl palmitate, ethylhexyl palmitate, isodecyl neopentanoate, C12–15 alcohols benzoate, diethylhexyl maleate, PPG-14 butyl ether, PPG-2 myristyl ether propionate, cetyl ricinoleate, cholesterol stearate, cholesterol isosterate, cholesterol acetate, jojoba oil, cocoa butter, shea butter, lanolin, lanolin esters. Examples of other suitable materials, including emollients, are disclosed in U.S. Pat. No. 4,919,934, to Deckner et at., issued Apr. 24, 1990; which is incorporated herein by reference in its entirety.

An especially useful group of emollients are the so-called "polar lipids" which contain hydrophilic moieties such as .hydroxy groups carbonyl groups and ether linkages. Preferred classes of these polar lipids include C10–20 alcohol monosorbitan esters, C10–20 alcohol sorbitan diesters, C10–20 alcohol sorbitan triesters, C10–20 alcohol sucrose monoesters, C10–20 alcohol sucrose diesters, C10–20 alcohol sucrose triesters, and C10–20 fatty alcohol esters of C2–C6 2-hydroxy acids. Nonlimiting examples of these polar lipids are sorbitan diisostearate, sorbitan dioleate, sorbitan distearate, sorbitan isosotearate, sorbitan laurate, sorbitan oleate, sorbitan palmitate, sorbitan sesquioleate, sorbitan sesquistearte, sorbitan stearate, sorbitan triiostearte, sorbitan trioleate, sorbitan tristeate, sucrose cocoate, sucrodilaurate, sucrose distearate, sucrose laurate, sucrose myristate, sucrose oleate, sucrose palmitate, sucrose ricinoleate, sucrose stearate, sucrose tribehenate, sucrose tristearate, myristyl lactate, stearyl lactate, isostearyl lactate, cetyl lactate, palmityl lactate, cocoyl lactate, and mixtures thereof. Other polar lipids are the C10–20 alkyl pidolates (i.e. pyrrolidone carboxylate esters, examples of which are myristyl pidolate, cetyl pidolate, lauryl pidolate, and stearyl pidolate). Yet other polar lipids are alkyl C1–3 esters of panthenol such as panthenyl triacetate (which is the triacetyl ester of panthenol). Especially preferred among the polar lipids are isostearyl lactate (available as Pationic Ill., from RITA Corp), sorbitan laurate (available as Arlacel 20 from ICI Americas), lauryl pyrrolidone carboxylic acid (available as lauryl pidolate from UCIB Corp.), panthenyl triacetate (available as D-panthenyl triacetate from Induchem), and mixtures thereof.

Also useful are silicones including non-volatile silicones such as dimethicone copolyol; dimethylpolysiloxane; diethylpolysiloxane; high molecular weight dimethicone (average molecular weight from about 200,000 to about 1,000,000 and, preferably, from about 300,000 to about 600,000) which can have various end-terminating groups such as hydroxyl, lower $C_1$–$C_3$ alkyl, lower $C_1$–$C_3$ alkoxy and the like; mixed $C_1$–$C_3$ alkyl polysiloxane (e.g., methylethylpolysiloxane); phenyl dimethicone and other aryl dimethicones; dimethiconol; fluorosilicones; and mixtures thereof.

Preferred are non-volatile silicones selected from the group consisting of dimethicone copolyol, dimethylpolysiloxane, diethylpolysiloxane, high molecular weight dimethicone, mixed $C_1$–$C_{30}$ alkyl polysiloxane, phenyl dimethicone, dimethiconol, and mixtures thereof. More preferred are non-volatile silicones selected from dimethicone, dimethiconol, mixed $C_1$–$C_{30}$ alkyl polysiloxane, and mixtures thereof. Especially preferred is dimethiconol which is a dimethyl silicone polymer terminated with hydroxyl groups. Dimethiconol is available as Q2-1401 Fluid, a solution of 13 percent ultra-high-viscosity dimethiconol in volatile cyclomethicone fluid as a carrier; as Q2-1403 Fluid, a solution of ultra-high-viscosity dimethiconol fluid in dimethicone (both sold by Dow Corning Corporation); and as other custom blends (e.g. 10% dimethiconol in dimethicone). Nonlimiting examples of silicones useful herein are described in U.S. Pat. No. 5,011,681, to Ciotti et al., issued Apr. 30, 1991, which has already been incorporated by reference.

Among the emollients preferred are those selected from the group consisting of dimethicone, dimethiconol, diisopropyl adipate, isopropyl myristate, myristyl myristate, cetyl ricinoleate, sorbitan distearte, sorbitan dilaurate, sorbitan stearate, sorbitan laurate, suscrose laurate, sucrose dilaurate, sodium isostearyl lactylate, lauryl pidolate, sorbitan stearate, panthenyl triacetate, and mixtures thereof. More preferred are those selected from the group consisting of sorbitan laurate, sucrose laurate, sodium isostearyl lactylate, lauryl pidolate, sorbitan stearate, panthenyl triacetate, and mixtures thereof. Most preferred are those selected from the group consisting of sodium isostearyl lactylate, lauryl pidolate, sorbitan stearate, panthenyl triacetate, and mixtures thereof.

Water

The compositions of the present invention comprise from about 35% to about 99.65%, more preferably from about 62.5% to about 98.5%, and most preferably from about 75% to about 97% water. Furthermore, the exact level of water in these compositions will also depend upon what other additional components as described below are added.

The compositions hereof will preferably be in the form of a stable single phase, most preferably a true solution. However the compositions hereof can be in the form of stable emulsions or coacervates containing one or more stable discontinuous phases dispersed throughout the aqueous, or water phase. Additionally, the compositions hereof can include multiple phases wherein the aqueous phase and the other phase or phases e.g. a lipid or emollient phase, form a separate layer. In order to be effective, such a composition must be well shaken or stirred prior to dispensing from the dispenser hereof. The phases must remain sufficiently dispersed or intermixed such that the foam produced upon activation of the dispenser contains effective levels of the humectant and emollient to condition the skin.

Preferably, the compositions hereof are essentially free of particulate (crystalline) matter. However, it is possible to include in the compositions hereof small particulate matter. The particulate matter should be of a sufficient shape and size so that it is capable of flowing through the screen of the pump dispenser (which is described in detail below) without unduly clogging the foam generation means of the dispenser during use. For instance, if typical usage of the product of the present invention involves one or two strokes of the pump, the particulate matter should allow flow of the composition through the porous foam generating means to form a foam for such use. Preferably multiple uses (e.g. two, three, five, ten, twenty, or more) can be practiced without necessitating cleaning of the porous foam generating means.

Additional Components

The compositions of the present invention can comprise the following additional components.

Anionic Surfactants

Preferably the compositions will be essentially free of anionic surfactants (i.e., less than 0.1%). However, the compositions of the present invention can further comprise a low level of one or more anionic surfactants. When an anionic surfactant is used, the level should be carefully chosen so as to maximize the foaming properties of the composition while striving to minimize any harshness trade-off. Typical levels of these anionic surfactants when used herein comprise from 0.1% to about 2.5%, more preferably from 0.1% to about 2%, and most preferably from 0.1% to about 1% of the compositions. A wide variety of anionic surfactants can be employed herein. Nonlimiting examples of anionic surfactants are described in *McCutcheon's, Detergents and Emulsifiers*, 1984 Annual, published by Allured Publishing Corporation, which is incorporated herein by reference. Also U.S. Pat. No. 3,929,678, to Laughlin et al., issued Dec. 30, 1975, discloses many other anionic as well as other surfactant types and is incorporated herein by reference in its entirety.

Preferred examples of anionic surfactants include the alkoyl isethionates, and the alkyl and alkyl ether sulfates. The alkoyl isethionates typically have the formula $RCO\text{-}OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof Preferred for used herein are ammonium cocoyl isethionate, sodium cocoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 20 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R_1\text{-}SO_3\text{-}M$$

wherein $R_1$ is chosen from the group consisting of a straight or branched chain, saturated aliphatic hydrocarbon radical having from about 8 to about 24, preferably about 12 to about 18, carbon atoms; and M is a cation. Still other anionic synthetic surfactants include the class designated as succinamates, olefin sulfonates having about 12 to about 24 carbon atoms, and b-alkyloxy alkane sulfonates.

Active Ingredients

The compositions of the present invention can contain a wide variety of other active ingredients for delivery to the skin or hair. The amount of active utilized in a particular formulation will vary depending upon the active chosen and the desired effect to be obtained. These actives typically comprise from abut 0.01% to about 20%, more preferably from about 0.05% to about 5%, and most preferably from about 0.1% to about 2% of the compositions herein. Mixtures of these actives can also be used. (It is to be understood herein that the various actives described below can provide, more than one benefit and can be appropriately classified under more than one category).

Nonlimiting examples of actives useful for delivery from the foam producing cleansing products are described below. For convenience, these actives have been classified into the nine categories listed below, however, this classification is in no way intended to limit an active to a particular class or function, or only to those particular classes or functions listed herein.

Anti-acne actives

Anti-acne actives preferred for use in the present invention include the keratolytics agents such as salicylic acid, sulfur, lactic acid, glycolic, pyruvic acid, urea, resorcinol, and N-acetylcysteine; retinoids such as retinoic acid (e.g., cis and trans); and its derivatives (e.g. retionol, retinyl palmitate) antibiotics and antimicrobials such as benzoyl peroxide, octopirox, erthromycin, zinc, tetracyclin, triclosan, azelaic acid and its derivatives, phenoxy ethanol and phenoxy proponol, ethylacetate, clindamycin and meclocycline; sebostats such as flavinoids; alpha and beta hydroxy acids; and bile salts such as scymnol sulfate and its derivatives, deoxycholate, and cholate. Preferred for use herein is salicylic acid.

Anti-wrinkle and anti-skin atrophy actives

Anti-wrinkle and anti-skin atrophy actives include the C2–C30 α-hydroxy acid (e.g. glycolic acid, lactic acid, 2-hydroxy butanoic acid, and the like), retinoic acid, salicylic acid, and skin peel agents (e.g. phenol, acetic acid). Preferred for use herein are glycolic acid, lactic acid, salicylic acid, and mixtures thereof.

Sunscreen actives

The exact amount of sunscreen active will vary depending upon the sunscreen or sunscreens chosen and the desired Sun Protection Factor (SPF) to be achieved. SPF is a commonly used measure of photoprotection of a sunscreen against erythema. The SPF is defined as the ratio of the ultraviolet energy required to produce minimal erythema on protected skin to that required to produce the same minimal erythema on unprotected skin in the same individual. See i Federal Registerl , Vol. 43, No. 166, pp. 38206–38269, Aug. 25, 1978, which is incorporated herein by reference in its entirety.

A wide variety of sunscreen actives are useful herein. These sunscreen actives include both organic compounds and their salts as well as inorganic particulate materials. Without being limited by theory, it is believed that sunscreen agents provide protection from ultraviolet radiation by one or more of the following mechanisms including absoprtion, scattering, and reflection of the ultraviolet radiation. Non-limiting examples of these sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; U.S. Pat. No. 5,160,731, to Sabatelli et al., issued Nov. 3, 1992; U.S. Pat. No. 5,138,089, to Sabatelli, issued Aug. 11, 1992; U.S. Pat. No. 5,041,282, to Sabatelli, issued Aug. 20, 1991; U.S. Pat. No. 4,999,186, to Sabatelli et al., issued Mar. 12, 1991; U.S. Pat. No. 4,937,370, to Sabatelli, issued Jun. 26, 1990; and Segarin, et al., at Chapter VIII, pages 189 et seq., of *Cosmetics Science and Technology*; all of these documents being incorporated herein by reference in their entirety.

Preferred among the sunscreen agents are those selected from the group consisting of 2-ethylhexyl p-methoxycinnamate, octyl salicylate, octocrylene, oxybenzone, 2-ethylhexyl N,N-dimethylaminobenzoate, p-aminobenzoic acid, 2-phenyl-benzimidazole-5-sulfonic acid, homomenthyl salicylate, DEA p-methoxycinnamate, 4,4'methoxy-t-butyldibenzoylmethane, 4-isopropyldibenzoylmethane, 3-(4-methylbenzylidene) camphor, 3-benzylidene camphor, 4-N,N-dimethylaminobenzoic acid ester with 2,4-dihydroxybenzophenone, 4-N,N-dimethylarninobenzoic acid ester with 2-hydroxy-4-(2-hydroxyethoxy) benzophenone, 4-N,N-dimethylaminobenzoic acid ester with 4-hydroxydibenzoyl- methane, 4-N,N-dimethylaminobenzoic acid ester with 4-(2-hydroxyethoxy) dibenzoylmethane, 4-N,N-di(2-ethylhexyl)aminobenzoic acid ester with 2,4-dihydroxybenzophenone, 4-N,N-di(2-ethylhexyl)aminobenzoic acid ester with 2-hydroxy-4-(2-hydroxyethoxy)benzophenone, 4-N,N-di(2-ethylhexyl) aminobenzoic acid ester with 4-hydroxydibenzoylmethane, 4-N,N-di(2-ethylhexyl)aminobenzoic acid ester with 4-(2-hydroxyethoxy)dibenzoylmethane, 4-N,N-(2-ethylhexyl) methylaminobenzoic acid ester with 2,4-dihydroxybenzophenone, 4-N,N-(2-ethylhexyl) methylaminobenzoic acid ester with 2-hydroxy-4-(2-hydroxyethoxy)benzophenone, 4-N,N-(2-ethylhexyl) methylaminobenzoic acid ester with 4-hydroxydibenzoylmethane, 4-N,N-(2-ethylhexyl) methylaminobenzoic acid ester with 4-(2-hydroxyethoxy) dibenzoylmethane, titanium dioxide, zinc oxide, iron oxide, and mixtures thereof.

More preferred for use in the compositions described herein are the sunscreen agents selected from the group consisting of 2-ethylhexyl N,N-dimethyl-p-aminobenzoate, 2-ethylhexyl p-methoxycinnamate, octocrylene, octyl salicylate, homomenthyl salicylate, p-aminobenzoic acid, oxybenzone, 2-phenylbenzimidazole-5-sulfonic acid, DEA p-methoxycinnamate, 4,4-methoxy-t-butyldibenzoylmethane, 4-isopropyl dibenzoylmethane, 3-(4-methylbenzylidene) camphor, 3-benzylidene camphor, titanium dioxide, zinc oxide, iron oxide, and mixtures thereof.

Most preferred for use in the compositions described herein are the sunscreen agents selected from the group consisting of ethylhexyl p-methoxycinnamate, octocrylene, octyl salicylate, oxybenzone, 2-phenylbenzimidazole-5-sulfonic acid, 4,4-methoxy-t-buyl-methoxydibenzoylmethane, 3-(4-methylbenzylidene) camphor, 3-benzylidene camphor, titanium dixoide, zinc oxide, iron oxide, and mixtures thereof.

Anti-Dandruff Actives

Anti-dandruff actives include octopirox, zinc pyrithione, selenium sulfide, and mixtures thereof.

Artificial Tanning actives

Artificial tanning actives include dihydroxyacetone, glyceraldehyde, tyrosine, ethyl tyrosine, phospho-DOPA, indoles and their derivatives, and mixtures thereof.

Nonsteroidal antiinflammatory actives

Non-steroidal anti-inflammatory actives (NSAIDS) can be selected from the following categories: propionic acid derivatives; acetic acid derivatives; fenamic acid derivatives; biphenylcarboxylic acid derivatives; and oxicams. All of these NSAIDS are fully described in the U.S. Pat. No. 4,985,459 to Sunshine et al., issued Jan. 15, 1991, incorporated by reference herein. Most preferred are the propionic NSAIDS including but not limited to aspirin, acetaminophen, ibuprofen, naproxen, benoxaprofen, fleurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucloxic acid, and mixtures thereof. Also useful are the steroidal anti-inflammatory drugs including hydrocortisone and the like.

Antipruritic actives

Antipruritic actives include pharmaceutically-acceptable salts of methdilizine and trimeprazine and mixtures thereof.

Topical anesthetic actives

Anesthetic actives include pharmaceutically-acceptable salts of lidocaine, bupivacaine, chlorprocaine, dibucaine, etidocaine, mepivacaine, tetracaine, dyclonine, hexylcaine, procaine, cocaine, ketamine, pramoxine, phenol, and mixtures thereof.

Antimicrobial actives

Antimicrobial actives include pharmaceutically-acceptable salts of b-lactam drugs, quinolone drugs, ciprofloxacin, norfloxacin, tetracycline, triclosan, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole and amanfadine. Antimicrobial drugs preferred for inclusion in compositions of the present invention include tetracycline hydrochloride, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, triclosan, octopirox, parachlorometa xylenol, nystatin, tolnafiate, clotrimazole, and mixtures thereof.

Miscellaneous Ingredients

A variety of additional ingredients can be incorporated into the compositions of the present invention. Non-limiting examples of these additional ingredients (which can include active ingredients as well as other ingredients) include vitamins and derivatives thereof (e.g tocopherol, tocopherol acetate, and the like); resins; gums; waxes (both naturally occurring and synthetic); skin penetration aids such as DMSO, 1-dodecylazacycloheptan-2-one (available as Azone from the Upjohn Co.) and the like; skin bleaching (or lightening) agents including but not limited to hydroquinone, kojic acid and sodium metabisulfite; antioxidants; chelators and sequestrants; and aesthetic components such as fragrances, pigments, colorings, essential oils, skin sensates, astringents, skin soothing agents, skin healing agents and the like, nonlimiting examples of these aesthetic components include panthenol and derivatives (e.g. ethyl panthenol), pantothenic acid and its derivatives, clove oil, menthol, camphor, eucalyptus oil, eugenol, menthyl lactate, witch hazel distillate, allantoin, bisabalol, dipotassium glycyrrhizinate and the like.

PHYSICAL PARAMETERS OF THE COMPOSITION

The foamable cleansing compositions of the present invention should have a liquid viscosity of from about 1 cps to about 300 cps, more preferably from about 20 cps to about 130 cps, and most preferably from about 50 cps to about 100 cps. However higher or lower viscosities can be used if the foam generated according to the present invention meets the foam parameters described below. Viscosities of the composition are measured before the composition is formed into a foam, using standard measuring techniques known to those of ordinary skill as formulation chemists. In particular, the viscosities of the composition as defined herein can be determined using a Brookfield Viscometer RVT (Brookfield Corp., Stoughton, Mass.), Spindle 1, at 100 rpm (for viscosities up to 100 cps) and Spindle 2 at 100 rpm (for viscosities above 100 cps), or by an equivalent method.

Physical Parameters of the Foam Generated

In general, a foam is generated by mixing a foamable liquid and a gas.

Foam Density

The foam generated from the products of the present invention preferably has a foam density of from about 0.01 gms/cm$^3$ to about 0.25 gms/cm$^3$, more preferably from about 0.05 gms/cm$^3$ to about 0.15 gms/cm$^3$, and most preferably from about 0.075 gms/cm$^3$ to about 0.125 gms/cm$^3$. Foam density is determined herein by weighing a given volume of foam immediately after dispensing. The ratio of the mass of the foamable liquid to the volume of air in such foam mixtures ranges from about 10–300 g of liquid per liter of air, more preferably about 20–130 g of liquid per liter of air, and most preferably about 30–90 g of liquid per liter of air.

Apparent Foam Viscosity

The apparent foam viscosity is at a shear rate of 10 reciprocal seconds (1/sec) for resultant foams is from about 500 cps to about 4,500 cps, more preferably is from about 1,000 cps to about 4,000 cps, and most preferably is from about 1,200 cps to about 3,000 cps. Apparent viscosity measurements of the foams are made immediately after dispensing using standard techniques and equipment, such as a Haake Rotoviscometer RV20 (Haake Corporation) using a cone-and-plate fixture (cone diameter of 41.74 mm, plate diameter of 45.00 mm, cone angle of $6.98 \times 10^{-2}$ rad and gap between the truncated apex of the cone and the plate of 0.175 mm). "Apparent viscosity" is used herein instead of just viscosity, since the viscosity value is calculated as the ratio of the stress to the applied shear rate, therefore, neglecting any effects of wall slip of the foam at the surfaces of the fixture.

Liquid Drainage

The liquid drainage from the foam is measured by introducing a certain mount of foam into a cubic fixture that is slightly tilted with respect to the perpendicular axis wherein the volume of liquid collected from the bottom of the cubic fixture over a specified amount of time is measured. Generally, well mixed foams containing more uniformly sized bubbles of smaller size produce less liquid drainage than poorly mixed foams containing less uniformly sized bubbles of larger size. In that respect, the liquid drainage test is considered a very informative measure of the quality of the foam.

NON-AEROSOL DISPENSER

DETAILED DESCRIPTION OF THE INVENTION

The manually actuable foam dispenser and the method of forming and dispensing foam in accordance with the present invention will generally be described with respect to manually-actuable pump foam dispensers and foam refining means. One of ordinary skill, however, will readily recognize that the inventions described herein can be readily utilized with other types of manually actuated foam dispensers, such as squeeze-bottle foam dispensers of the type generally described in Japanese Laid-Open Patent No. Showa 60-148468, as well as aerosol-type foam dispensers.

As used in the following discussion the velocity of a foam mixture through a conduit, $V_1$, is a calculated average velocity expressed in cm/sec and is determined by dividing the volumetric flow rate of foam generated by a foam-generating means, Q, in $cm^3$/sec, by the cross-sectional area (or flow area) of the conduit, $A_1$, in $cm^2$. The velocity of a foam mixture through the foam refining means, $V_2$, is a calculated average velocity expressed in cm/sec and is determined by dividing the same volumetric flow rate of the foam, Q, in $cm^3$/sec, by the open area of the foam refining means, $A_2$, in $cm^2$. In the case that the total area of the screen, $A_2$, is equal to the cross-sectional area of the conduit just prior to it, $A_1$, then $A_2$ is equal to the multiple of the percentage open area of the screen, k, and the cross-sectional area of the conduit just prior to the screen, $A_1$ (i.e., $A_2=kA_1$). For the purposes of the present discussion, the term "average velocity" will herein be simply "velocity". The actual velocity, $V_2$, may vary, for example, as the foam is compressed while passing through the passageways in the screen (i.e., Q changes as the foam passes through the foam refining means since it contains a large volume of gas, which is a compressible fluid). However, the calculated velocity $V_2$ is the most practical way of estimating the actual velocity of the moving foam and it is sufficiently accurate and reproducible to carry out the invention described herein.

Also discussed herein, the passageway size of the foam refining means, as measured perpendicular to its axis, is the length of the side of a square which has the same area as that of the particular passageway. Also, as used herein, a foam refining means having a given passageway size will preferably have less than about 5% of its total flow area comprised of passageways of greater than the given passageway size, preferably less than about 1%.

Figure 9:
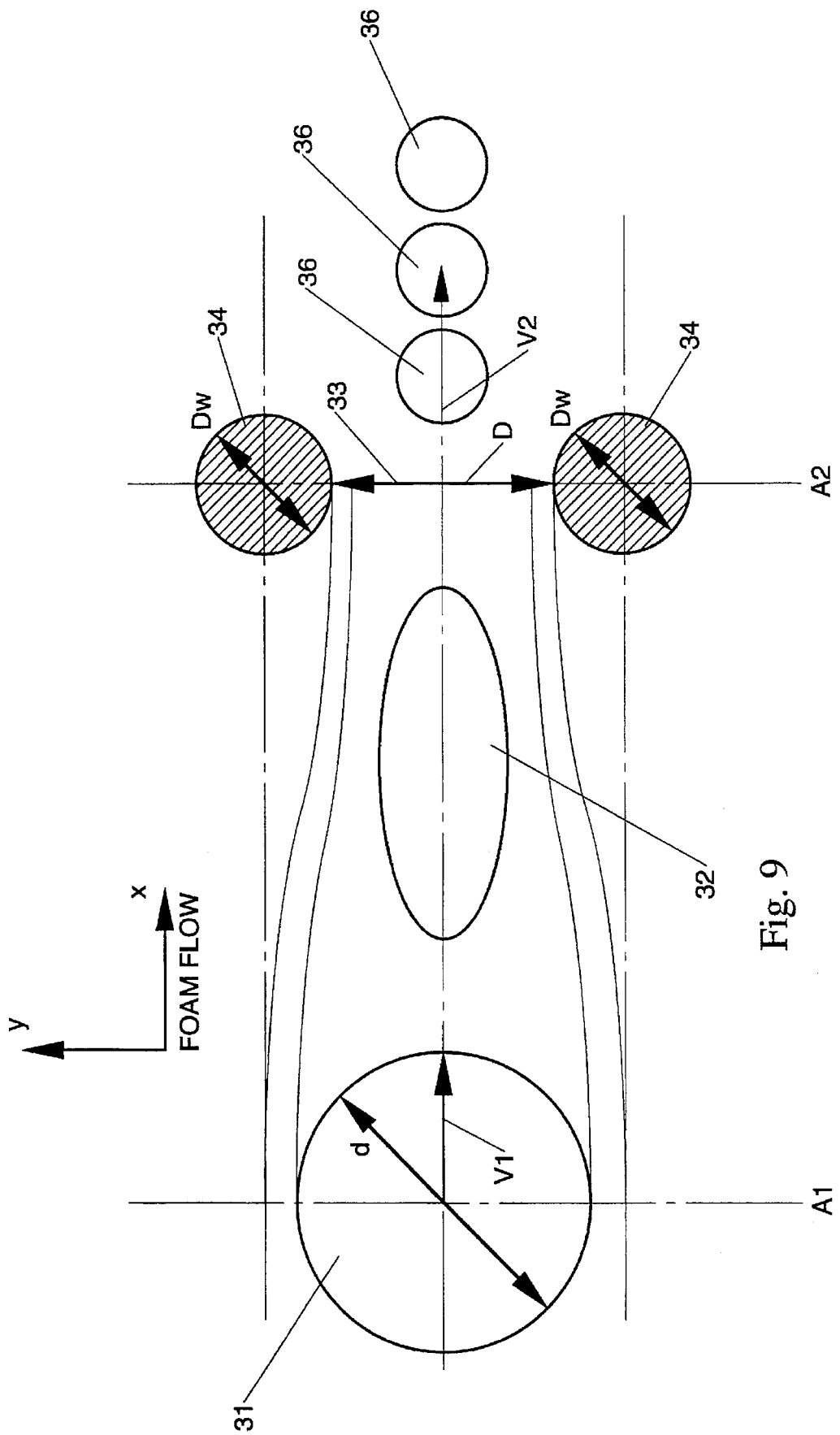
FIG. 9 shows a microscopic cross-sectional view (not in scale) of a single bubble undergoing extension and break-up into smaller bubbles while passing through a passageway of a foam refining means.
Figure 10:
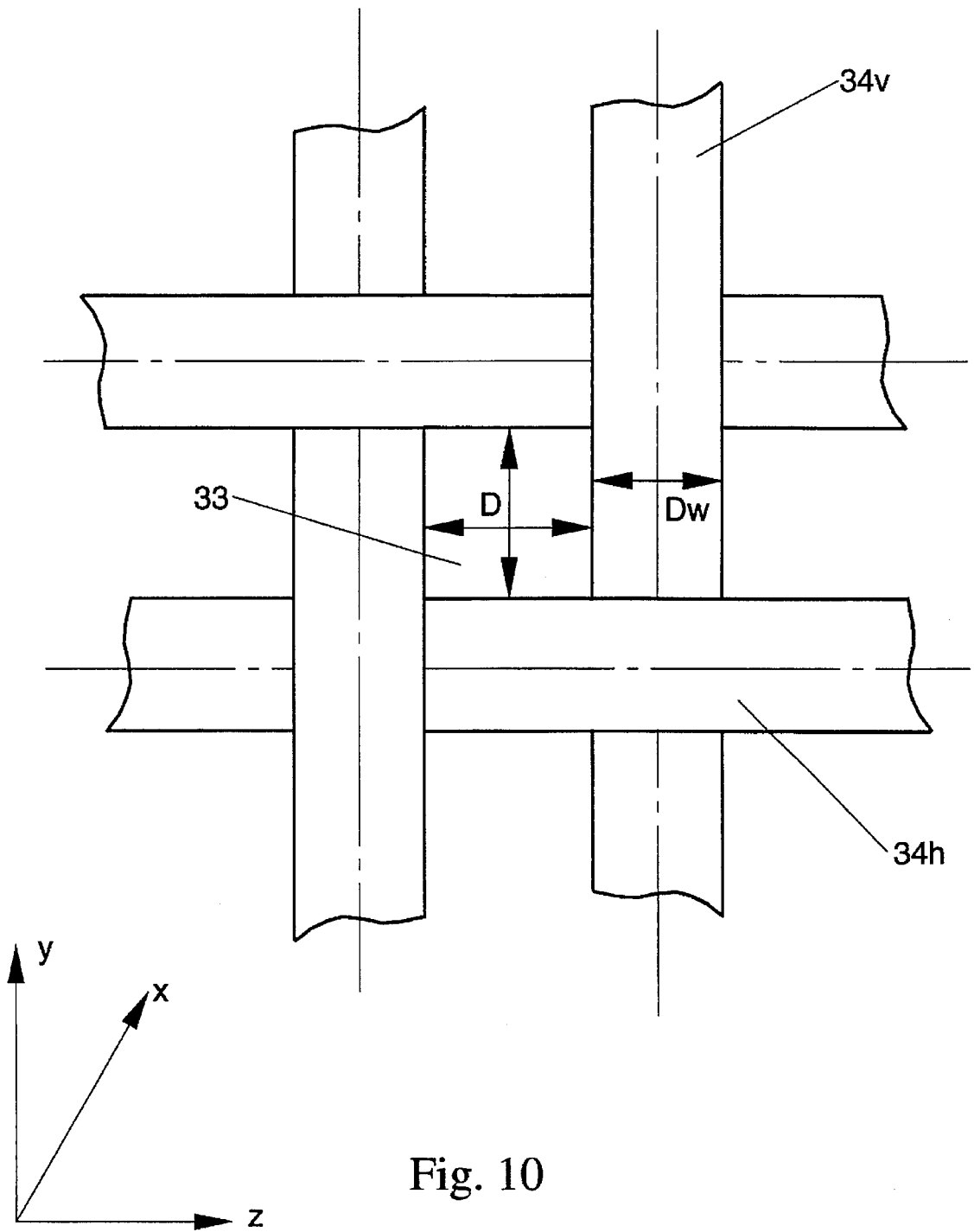
FIG. 10 shows the frontal view of a screen passageway of a foam refining screen.

Foams containing relatively large diameter bubbles can be refined by forcing said foams through various foam refining means including screens, porous frits, porous media, static mixers and combinations thereof. In FIG. 9 a large diameter bubble 31, as makes up in part the foam, is shown approaching the foam refining means 30 of FIG. 1 along the x axis. FIG. 9 is drawn for demonstration purposes only, and is not to scale, nor does it show the actual concentration of bubbles which comprise said foam. As bubble 31 travels towards the screen 30, it undergoes deformation by a combination of extensional and shear fields existing between points $A_1$ to $A_2$ of FIG. 9 and it becomes the extended bubble 32. This extended bubble 32 undergoes further extension as it passes through the passageway 33. FIG. 10 shows a frontal view of passageway 33, which is the void created by the intersection of horizontal wires 34h and vertical wires 34v. Furthermore, the effectiveness of said foam refining means depends on its ability to create the required extensional and shear fields for bubble break-up, and the strain rates generated by each of these fields, since their individual effectiveness is different. Predictions of the conditions which lead to bubble break-up are in part based on experimental work published by Karam, H. J., and I. C. Bellinger, *Deformation and Breakup of Liquid Droplets in a Simple Shear Field*, Ind. Engng Chem. Fundam., 7, 576–581(1968), and Grace, H. P., *Dispersion Phenomena in High Viscosity Immiscible Fluid Systems and Application of Static Mixers as Dispersion Devices in Such Systems*, Chem. Engng Commun., 14, 225–277 (1982); both herein incorporated by reference. Although Grace's work pertains to single drop or bubble deformation and break-up in (rotational or simple) shear and planar extensional (irrotational or pure shear) fields, the conditions which lead to bubble break-up in a concentrated dispersion of bubbles in a liquid continuous phase subjected to a combination of rotational and irrotational shear fields can still be applied, at least in a qualitative sense.

The following parameters are used by Grace and are also used in the present discussion:

*Viscosity Ratio* is the ratio of the viscosity of the dispersed phase, in this case air, to the viscosity of the continuous phase, that is the foamable liquid. The viscosity of air at 25° C. and pressure of 1 atm is taken from tables available in the literature, and is equal to $1.8 \times 10^{-2}$ cps. Typical values of the viscosity ratio for the purposes of the present invention range from about $1.8 \times 10^{-2}$ to about $6.0 \times 10^{-5}$ (for the viscosity of the foamable liquid ranging from about 1 cps to about 300 cps), more preferably from about $9.0 \times 10^{-4}$ to about $1.4 \times 10^{-4}$ (for the viscosity of the foamable liquid ranging from about 20 cps to about 130 cps), and most preferably from about $3.6 \times 10^{-4}$ to about $1.8 \times 10^{-4}$ (for the viscosity of the foamable liquid ranging from about 50 cps to about 100 cps).

*Critical Shear Rate* is the critical shear gradient applied upon a bubble below which bubble break-up cannot be achieved. Although rotational and irrotational shear fields require different critical shear rates for bubble break-up (the rotational shear rate being much higher than the irrotational shear rate for low viscosity ratios; see FIG. 19 of Grace's work), for simplicity, shear rate as used hereinafter will denote either rotational or irrotational shear rates.

*Critical Burst Time* is the time required under critical shear rate for bubble break-up to take place.

*Critical Draw Ratio* is the necessary extension or deformation of the bubble at the critical shear rate for said bubble's break-up. The draw ratio is defined as the length of the extended bubble over the original bubble diameter.

For bubble break-up to occur at the critical shear rate, the following conditions should be met: (a) the bubble should experience the critical shear rate for time at least equal to its critical burst time, and (b) the bubble's draw ratio should be at least equal to its critical draw ratio. The specific values of (a) and (b) above can be estimated from Grace's work (specifically FIGS. 5, 9 and 10 for rotational shear fields and FIGS. 18, 22 and 24 for irrotational shear fields) for a certain viscosity ratio, dynamic surface tension of the foamable liquid, and original bubble diameter. When the actual shear rate exceeds the critical shear rate, then the bubble burst time is shortened and falls below the critical burst time and the bubble's draw ratio becomes greater than the corresponding bubble's critical draw ratio (see FIGS. 13 and 11 of Grace's work respectively).

Foam flows through a foam refining means, such as a screen, wherein the bubbles approaching the opening 33 of the screen will be extended forming a slender bubbles 32. Extension occurs because of the higher velocity $V_2$ over $V_1$ along the x axis, and the velocity differences along the y and z axes. $V_2$ is based on the open area of all passageways (equal to the open area of the screen, also called flow area of the screen), $A_2$, which is equal to the total number of passageways, N, times the open area of one passageway, $a_2$. The open area of the passageways is considered to be of a square shape and equal to $D^2$, where D is the width or height of the passageway. $V_1$ is based on the total area upstream from the screen, $A_1$ (also called the cross-sectional area of the conduit, or the flow area of the conduit) which is equal to the total number of passageways, N, times the area corresponding to one passageway, $a_1$. The area, $a_1$, corresponding to each passageway, is equal to, $(D+D_w)^2$, $D_w$ being the diameter of the wire comprising the screen. The ratio of the open area of the screen, $A_2$, and the cross-sectional area of the conduit $A_1$ is typically from about 15% to about 50%. Typically, the velocity ratio of $V_2$ to $V_1$, which is equal to the ratio of $A_1$ to $A_2$, is from about 2.0 to about 6.7, if the compressibility effects on the velocity are neglected. Thus, when the shear rate is at least equal to the critical shear rate, and the bubble's residence time and draw ratio in the high shear region is at least equal to the corresponding values at the conditions of the actual shear rate the bubble bursts producing a number of smaller daughter bubbles.

The viscosity and dynamic surface tension of the foamable liquid, viscosity of the gas, flow area of the conduit, flow area of the refining means, diameter of the original bubble, and pump actuation dynamics (volumetric flow rate of the foam through the conduit) all play an important role for making quality foams. Based on the above mentioned conditions for bubble break-up, for all other conditions remaining the same (e.g. foamable liquid composition and its foamability), and neglecting any effect of the conduit flow area and its geometry on the bubble size and its distribution in the upstream position of the foam refining means, one expects that an increase of the conduit flow area results in increased residence time of the bubble in the high shear area upstream of the screen opening. Consequently, and to the extent that the shear rate exceeds the corresponding critical value and the conditions for the burst time and draw ratio are met, one expects that a bubble in the larger-conduit-flow-area case will break-up, whereas the same bubble in the smaller-conduit-flow-area case will not break since the condition for the burst time is not met.

Of course, a large increase of the conduit flow area might result in an actual shear rate lower than the corresponding critical value, in which case bubble break-up will not occur. Similarly, if a bubble of a certain diameter does not break when the viscosity of the foamable liquid is increased (the condition for the draw ratio is not met), an increase of the flow area of the conduit might result in a decrease of the ratio of the actual to the critical shear rates. This in turn decreases the required draw ratio (see FIG. 11 of Grace's work) and the probability of bubble break-up increases.

For a given conduit flow area, the effect of the foam volumetric flow rate depends on the characteristics of the pump dispenser and the actuation dynamics of the user of the pump. Said effect of the foam volumetric flow rate can be estimated based on the above mentioned conditions. Thus, for a range of volumetric flow rates one expects that all conditions are met, which results in a high quality foam. However, at either low or high volumetric flow rates one or more of the conditions are not met (at least the shear rate condition for the low volumetric flow rate case, and at least the burst time condition for the high volumetric flow rate case), which results in a poor quality foam.

The effect of the viscosity of the foamable liquid on the above mentioned range for high quality foam is understood from the theoretical approach discussed above. The higher the viscosity of the foamable liquid, the smaller the viscosity ratio. The smaller this ratio, the lower the critical shear rate. The lower the critical shear rate, the higher the ratio of actual to critical shear rates. The higher this ratio of shear rates, the higher the draw ratio, and the lower the burst time. Consequently, one expects that the volumetric flow rate range for high quality foam shifts lower for higher viscosity foamable liquids as compared to lower viscosity foamable liquids.

Finally, the effect of the screen itself can be better understood if application of the above conditions is made. A low-mesh (or coarse-mesh) screen is expected to generate low shear rate, and thus even if this shear rate exceeds the corresponding critical value, the ratio of the actual to critical values is expected to be low and thus the burst time is expected to be long. On the other hand, a very high-mesh (or fine-mesh) screen is expected to generate high shear rates, but not to meet the burst time condition.

The velocity of the foam through the foam refining means, $V_2$, can be considered to include all the above mentioned parameters, i.e., shear rate, residence time, and draw ratio. In general, higher velocity corresponds to higher values of shear rate and draw ratio, and lower residence time. For example, when $V_2$ is greater than $V_{2,max}$, then the residence time of the bubble in the high shear region is shorter than it needs to be for bursting, which bursting time corresponds to the ratio of the actual to the critical shear rates. Conversely, when $V_2$ is lower than $V_{2,min}$, then (1) either the actual shear rate does not exceed the critical shear rate, or (2) that the actual shear rate exceeds the critical shear rate, but, the residence time (and/or draw ratio) of the bubble in the high shear region is lower than the required burst time (and/or draw ratio). In other words, there is a range of foam velocity through the foam refining means, from $V_{2,min}$ to $V_{2,max}$ that is necessary for dispensing high quality foam. In the present invention the $V_2$ values necessary to achieve production of improved foam in context of the foam dispenser disclosed herein are preferably from about 15 cm/sec to about 400 cm/sec, and more preferably from about 20 cm/sec to about 350 cm/sec.

The quality of the foam is also affected by using additional foam refining means. For example, foams produced using a coarse-mesh screen 7 in the inlet conduit 5 of the foam dispensing nozzle (the inlet conduit is also called the stem of the nozzle) with a fine-mesh screen 30 close to the discharge end of the nozzle can be improved by the addition of either an intermediate (third) screen (screen 38 of FIG. 7) or a static mixer (static mixer 39 of FIG. 8) between the two original screens.

The nozzles containing an additional intermediate screen (i.e., three-screen nozzles) are capable of dispensing foams which are more persistent (i.e., with improved percent liquid drainage values) than foams generated from a two-screen nozzle. The selection of the intermediate screen, however, is critical for the production of distinguishable foams. For example, a three-screen nozzle with screens having mesh sizes corresponding to 100T, 183 by 264 (this is a dual mesh size screen, i.e., its mesh sizes along the z and y axes of FIG. 10 are not the same, in distinction with the square mesh size screen, wherein its mesh sizes along the z and y axes of FIG. 10 are the same), and 355T, dispenses a more persistent foam than a three-screen nozzle with screens of sizes 100T, 305, and 355T, using a 19.0 cps foamable liquid. The difference is believed attributable to the conditions for bubble break-up achieved by each screen. The 305 mesh intermediate screen has 41% open area. Such an open area is expected to reduce the ratio of actual to critical shear rates and consequently to increase the burst time and reduce the draw ratio. Based on the above, the probability of bubble break-up for larger bubbles is greater than that for smaller bubbles. Consequently, the liquid drainage data should be less sensitive to actuation dynamics, for the three-screen nozzle than for the corresponding two screen-nozzle.

On the other hand, the 183 by 264 mesh screen is expected to cause bubble break-up since its low percentage open area (21%) increases the ratio of actual to critical shear rates and consequently reduces the burst time and increases the draw ratio. Furthermore, the characteristics of the 183 by 264 intermediate screen, and the 355T discharge screen are similar, so that the shape of the curves for liquid drainage versus actuation dynamics is expected to be similar to one another. Consequently, any screen with mesh size between those of the stem and the discharge screens cannot necessarily be beneficial to the dispensed foam.

The nozzle which contains a static mixer between the stem and the discharge screens can also dispense high quality foams from foamable liquids. The dispensed foams are more persistent that those from typical two-screen nozzles and less sensitive to actuation dynamics (i.e., liquid drainage and foam thickness data is constant and does not depend on how fast or slow the user actuates the dispenser, for a wide range of actuation dynamics). The static mixer provides shear rate and residence time for bubble break-up, it also breaks bubbles by the mechanism of flow division and finally, it homogenizes the dispersion of bubbles into the continuous liquid phase. As a result the intermediate foam which emerges out of the static mixer is expected to be homogeneous and to contain bubbles with a more uniform bubble size distribution and smaller average bubble size. Note that a smaller bubble requires higher critical shear rate and lower burst time and draw ratio to break-up, so that its burst is easier to achieve, as long as the actual shear rate exceeds the critical one. Finally, the discharge screen breaks the bubbles of the intermediate foam even further. The more elements that a static mixer system has, the better the bubble break-up and homogenization are achieved. However, there is a practical limit on the number of elements, since the length of the nozzle cannot exceed a certain limit and the pressure drop increases with the number of elements.

The effect of the pressure distribution along the flow path of the foam was not discussed, since an increased pressure drop along the flow path is expected to increase the strain rates that the bubbles experience and reduce the residence times of the bubbles. These phenomena have been discussed above in the context of the conditions for break-up and will not be further discussed. Finally, when comparing the present invention with prior art dispensers one should utilize the same composition of foamable liquids. The reason for this being that variations of the composition of the foamable liquid (e.g. type of surface-active agents) can be responsible for variations in the quality of the foam even when using the same dispenser.

FOAM DISPENSING NOZZLE

The present invention also includes an improved foam refining nozzle for forming stable homogeneous foam from a mixture of a foamable liquid and a gas, otherwise known as an intermediate foam. Such improved foam refining nozzle can be formed integrally with the manually-actuable foam, as mentioned above, or, as is described below, it can be sealably attached to a separate manually-actuable foam pump. Although the nozzle is described below as being attached to a manually-actuable foam pump, it is within the ability of persons skilled in this art to adapt the present invention for use with other foam dispensers, such as squeeze-dispensers and aerosol dispensers.

The improved foam dispensing nozzle comprises:
(a) an inlet conduit for receiving an intermediate foam consisting of a mixture of a foamable liquid and a gas at a volumetric flow rate sufficiently high that it will produce an average incoming intermediate foam velocity which is too great to permit effective bubble bursting to put said foam in a final foam as said foam passes through at least one downstream foam refining means having a plurality of passageways therethrough; and
(b) a velocity decreasing means placing said inlet conduit in fluid communication with a foam refining means, wherein said velocity decreasing means lowers the average velocity of said intermediate foam so when said foam passes through said foam refining means it is at a velocity no greater than about 300 cm/sec.

In the practice of this aspect of the present invention, the intermediate foam can be generated and discharged to the nozzle by any conventional means, although the use of a manually-actuable foam pump is preferred.

Figure 1:
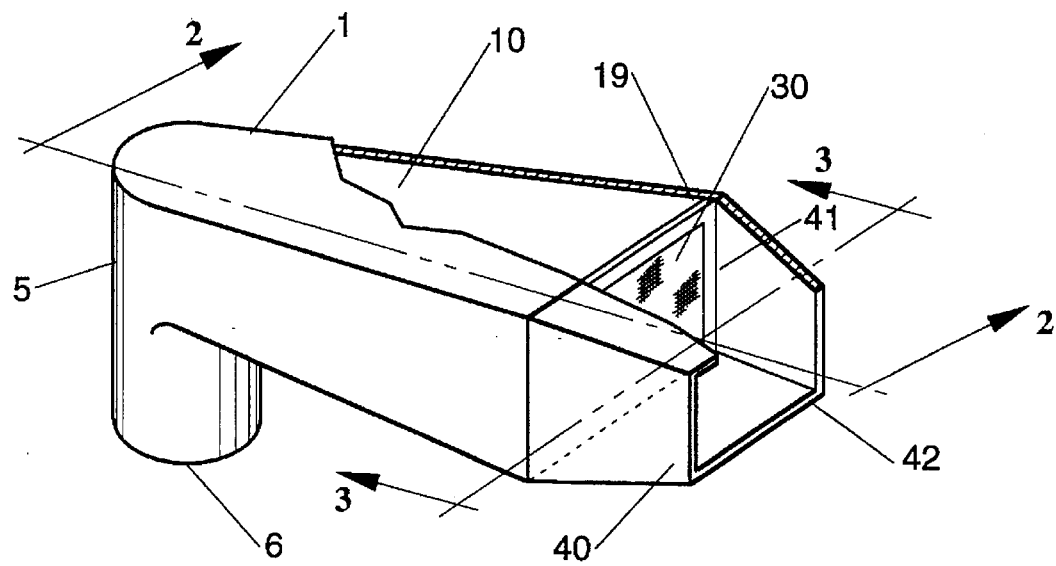
FIG. 1 shows a perspective view with a partial cutaway of one embodiment of a foam dispensing nozzle according to the present invention.

FIG. 1 shows an embodiment of the improved foam refining nozzle 1 of the present invention.

(a) Inlet Conduit

The inlet conduit 5 provides fluid flow transition from a discharge of a foam pump means, such as a pump discharge tube (not shown). In FIG. 1, inlet conduit 5 has circular cross section to fit snugly and sealably over the cylindrical pump discharge tube of a foam pump. The inlet conduit 5 can also be any other useful shape, size, length, or configuration which serves the purpose of adapting the nozzle 1 to a foam pump. Optionally, a foam homogenizing screen 7, as previously described, can be mounted inside the inlet conduit to improve the homogeneity of the foam mixture entering the nozzle 1. This screen has an effective pore opening size of about 0.150 mm to 0.200 mm, and is typically a 100T mesh-type screen.

(b) Expanded Conduit and Foam Refining Means

A preferred embodiment herein provides a foam refining nozzle wherein the velocity decreasing means comprises a volume expanding means. The volume expanding means causes the velocity of the intermediate foam to be reduced as the advancing foam expands in the plane perpendicular to the direction of flow. The expanded conduit 10 is in fluid flow communication only with the inlet to the nozzle and with the foam refining means 30, and provides for passage of the entire foam mixture from the inlet of the nozzle to the screen. There is no intention that additional foamable liquid or air be introduced into the expanded conduit, or for any portion of the foamable mixture to be discharged from the expanded conduit prior to passage of the mixture through the screen.

The expanded conduit 10 has a cross-sectional area at its outlet 19 which is at least larger than the cross-sectional area of the inlet 6. As used herein, the cross-sectional area of the inlet 6 or the outlet 19, or at any point along a conduit, is the area of a plane through which the foam mixture can pass which is, perpendicular to the flow of fluid through such area. Preferably, the ratio of the cross-sectional areas of outlet of the expanded conduit 19 to inlet 6 of the inlet conduit is from about 2:1 to about 12:1, more preferably from about 2:1 to about 8:1, and most preferably from about 4:1 to about 8:1. The cross-sectional shape of the expanded conduit 10 can be square, rectangular, oval, or any other shape that provides efficient flow of the air/liquid mixture from the inlet conduit 5 to the porous foam refining means 30. A typical cross-sectional shape is a rectangle having a height to width ratio of from about 1:1.5 to about 1:2. Though ordinarily the cross-sectional shape along the entire length of the expanded conduit 10 will not change, there is no limitation to changing from, for example, a rectangular shape near the inlet portion 11 of conduit 10 to oval shape near the outlet 19. The selection of the specific shape and geometry of the expansion conduit 10 will also take into account its aesthetic design and functionality (that is, how easily and conveniently the pump form is operated). Preferably, the cross-sectional area along the expanded conduit 10 will be increased gradually, from the inlet to the outlet 19. However, the expanded conduit can also be constructed such that the expansion of the conduit occurs abruptly anywhere along the length of the expanded conduit, such as at the inlet 11 or at the outlet 19.

Figure 2A:
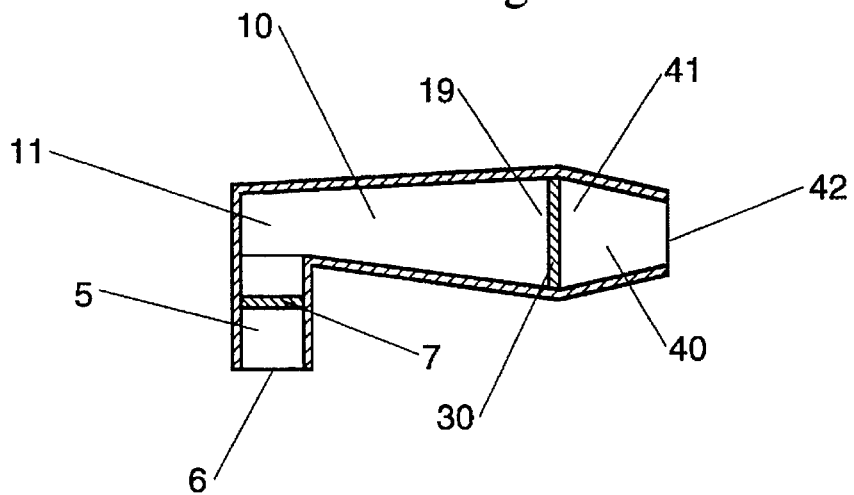
FIG. 2a shows a sectional view of the foam dispensing nozzle of FIG. 1 through line 2—2.
Figure 2B:
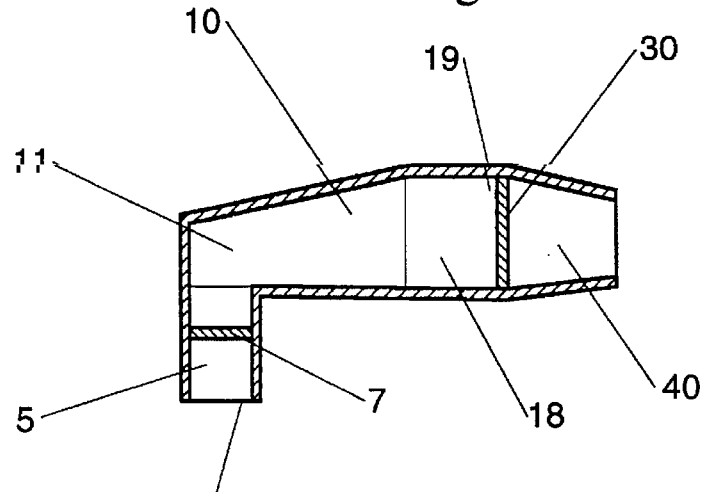
FIG. 2b shows a sectional view of an alternative embodiment of FIG. 1 through line 2—2.
Figure 3:
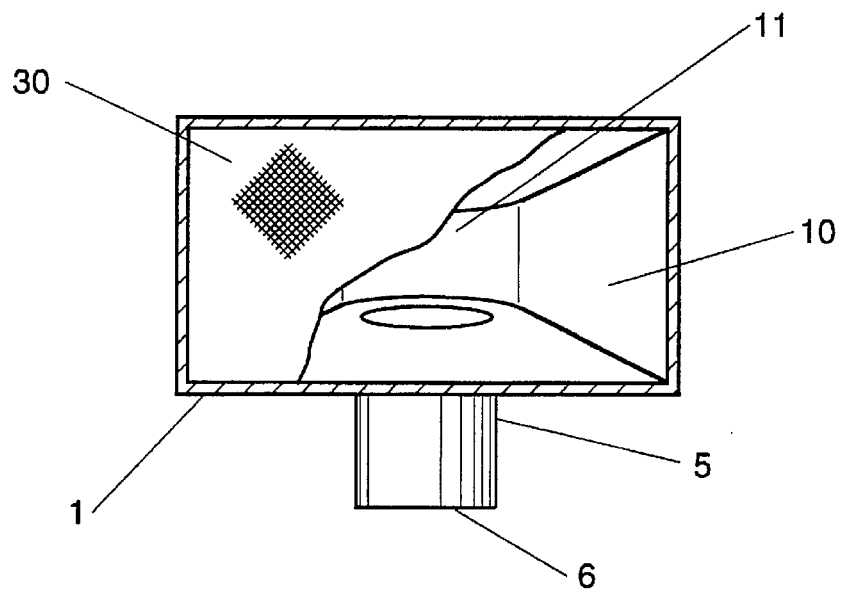
FIG. 3 shows a sectional view of the foam dispensing nozzle of FIG. 1 through line 3—3.

The outlet 19 of the expanded conduit 10 is in fluid communication with the foam refining means 30. The outlet 19 can be the terminus of the expanding cross section of the conduit 10, as shown in FIG. 2a and FIG. 3, or can be the outlet of connecting portion 18 as shown in FIG. 2b.

Figure 5:
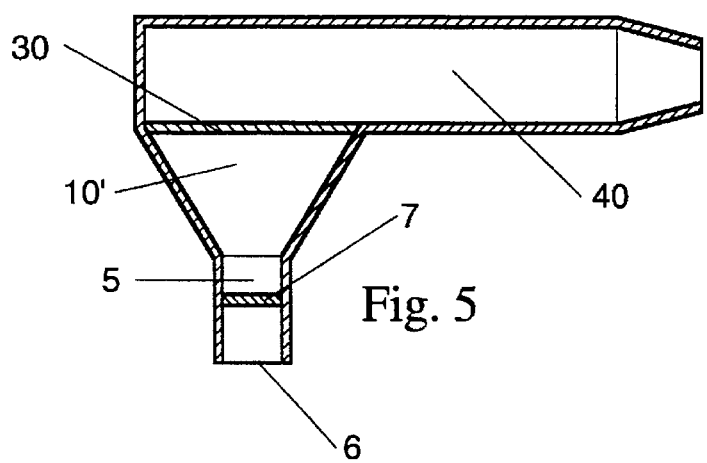
FIG. 5 shows a sectional view of still another embodiment of a foam dispensing nozzle according to the present invention.

Depending on the type of foam dispensing package used and the desired application, the expanded conduit 10 can be oriented in either the horizontal (as shown in FIG. 1) or the vertical (as shown in FIG. 5), or an orientation in between. In normal use, a manually-actuated pump foam dispenser is oriented horizontally in the expanded conduit 10.

The mixture of foamable liquid and air exits at a reduced velocity from the expanded conduit 10, and enters and passes through a porous foam refining means 30. The total cross-sectional area of the porous foam refining means 30 through which the foam mixture can flow is preferably substantially the same as the cross-sectional area of the outlet 19.

The refining means described herein above is generally sufficient for use with the present embodiment. The refining means is preferably a meshed screen. The refining screen 30 has a plurality of uniformly-sized, and evenly distributed passageways having a maximum dimension typically less than about 0.175 mm as measured perpendicular to its axis, preferably in the range of about 0.020 mm to about 0.120 mm, more preferably in the range of about 0.035 mm to about 0.080 mm, and most preferably in the range of about 0.035 mm to about 0.060 mm.

The total refining screen area can range from about 0.5 cm$^2$ to about 10 cm$^2$, more preferably from about 1 cm$^2$ to about 2 cm$^2$.

After the foam mixture passes through refining screen 30 and a final foam is generated, the final foam may be discharged through an optional outlet conduit 40. A short, converging optional outlet conduit 40 is typically used with the present invention, having an inlet 41 communicating with and adjacent to the outlet surface of the refining screen 30, and an outlet 42 for discharging the foam to the user's hand or other implement for use. A converging discharge 40 provides the discharged foam with increased velocity and momentum to satisfy the consumer's desire and expectation, and to provide a clean, sharp break of the dispensed foam at the end of the dispensing stroke from the foam which remains inside the dispensing device. The shape and convergence of the discharge conduit is selected to avoid diminishing the quality of the foam that has been generated. Typically, the outlet 42 is an opening of from about 0.5 cm$^2$ to about 2 cm$^2$. The configuration of the discharge conduit and the shape of the opening of the outlet 42 can be selected to satisfy both aesthetic and function needs for the foam dispenser.

The optional outlet conduit can be a separate component which is sealably and either permanently or removably attached to the outlet 19 of the expanded conduit 10. In the manufacture of the nozzle 1, the optional outlet conduit 40 is usually attached after the refining screen 30 has been positioned or secured in place. The screen can be secured to either the expanded conduit 10, or to the optional outlet conduit 40, or it can simply be held in place between the two pieces when the optional outlet conduit 40 is attached to the expanded conduit 10.

Figure 6:
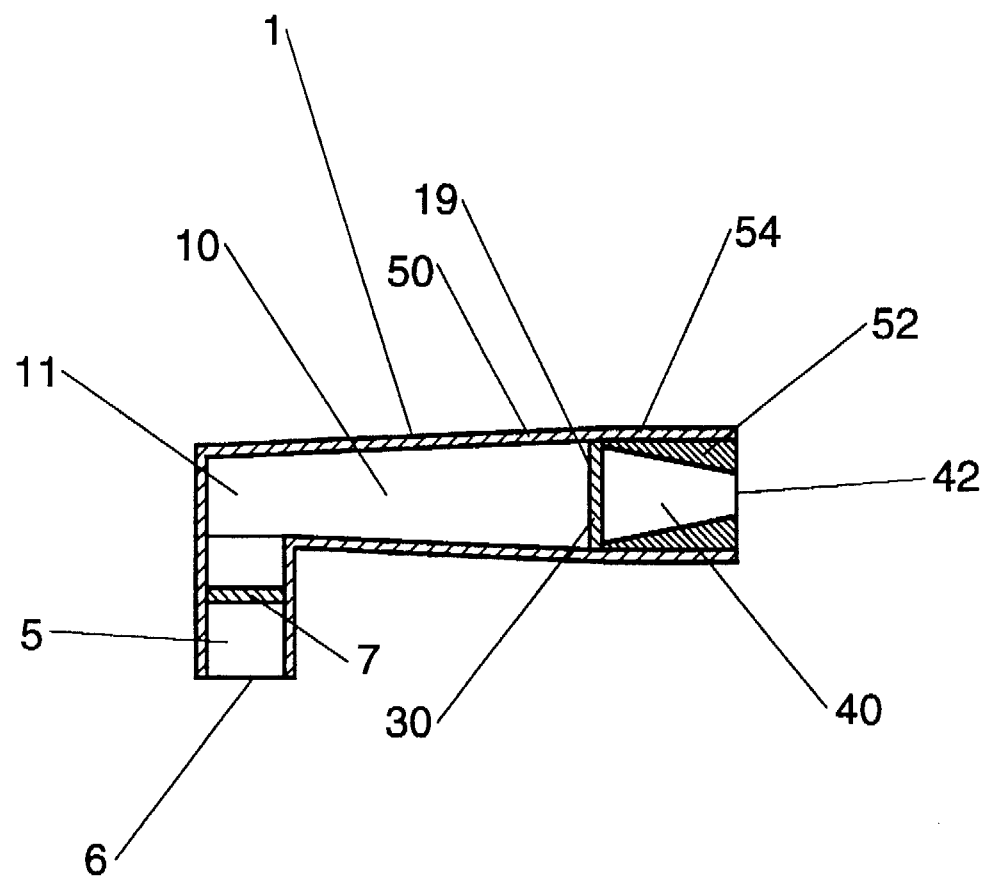
FIG. 6 shows a sectional view of yet another embodiment of a foam dispensing nozzle of the present invention.

In a preferred embodiment, a foam dispensing nozzle as shown in FIG. 6 is made by attaching the refining screen 30 to the optional outlet conduit 40 at its inlet end 41, thereby forming a screen insert 52. The housing 50 of the nozzle 1 extends beyond the expanded conduit outlet 19 to form an insert sleeve 54. The screen insert 52 is then inserted into and sealably affixed within the insert sleeve 54 such that the screen 30 is positioned at the expanded conduit outlet 19.

The optional outlet conduit can also be made integral with the nozzle 1. In this case, the screen is preferably inserted into position through a slot in the wall of the device at expanded conduit outlet 19 and then sealed and secured in place.

The inlet conduit 5, the expanded conduit 10, and the optional outlet conduit 40, as well as the remaining housing of nozzle 1, can be made by conventional molding or casting methods, and are most conveniently a plastic material, such as polyester, polypropylene, polyethylene, high density polyethylene, or linear low density polyethylene. Polypropylene is preferred.

MANUALLY-ACTUABLE FOAM DISPENSERS

The present invention embodies various manually actuable foam dispensers including aerosol dispensers, squeeze dispensers and pump dispensers. Preferred are user-actuable squeeze dispensers and pump dispensers, most preferably pump dispensers.

The manually-actuable foam dispensers of the present invention are capable of producing and dispensing a high quality final foam from a foamable liquid and a gas, said foam being comprised of bubbles having a number-average diameter of about $D_1$, said dispenser comprising:

(a) a manually-actuable means for mixing a quantity of said foamable liquid with a quantity of said gas to produce an intermediate foam which comprises bubbles having a number-average diameter greater than about $D_1$ and a wider bubble size distribution than the final foam, at a volumetric flow rate Q which is dependent upon the speed of actuation of said manually-actuable means by the user; and (b) a foam dispensing nozzle comprising a conduit in fluid communication with said manually-actuable means for receiving the intermediate foam from said manually-actuable means; and at least one foam refining means located in said conduit, said foam refining means comprising a plurality of substantially uniformly-sized and evenly distributed passageways; wherein said intermediate foam passes through said passageways at a velocity, $V_2$, falling within the range of a minimum velocity, $V_{2,min}$, and a maximum velocity, $V_{2,max}$, wherein the conditions needed to cause bursting of said bubbles having a diameter larger than about $D_1$ are met.

(a) Manually-Actuable Means

The manually-actuable means for mixing a quantity of said foamable liquid with said gas to produce a foam comprised of bubbles having a number-average diameter larger than about $D_1$ and a wider bubble size distribution than the final foam, is preferably capable of discharging the resulting foam at a volumetric flow rate in the range of about 4 cm³/sec to about 140 cm³/sec, and more preferably about 14 cm³/sec to about 40 cm³/sec, depending upon the speed of actuation of the means by the user. This range of volumetric flow rates is normally about right for skin and hair care products and cleaning products, such as hand soap, shampoo, body soap, hair mousse, shaving foam and kitchen cleanser. Among the said means used in the present invention are those well known in the art for bringing the liquid and air together to be mixed into a foam, e.g., aerosol canisters, deformable reservoirs, and pump foamers which are squeezed or actuated by the user to express the foamable liquid and air into a mixing chamber. Pump foamers are preferably used herein, most preferably pump foamers which are manually-actuated by applying force to the top of the pump stem, thereby mixing liquid and gas with each stroke. Examples of these particularly preferred pump foamers are shown in Japanese Laid-Open Utility Model No. Hei 3-7963 (Daiwa Can Co., Ltd.). This publication discloses a dual chamber foam dispenser, wherein the foamable liquid and the air are separately but simultaneously pumped into the mixing chamber, thereby providing a consistent ratio and quantity of liquid and air with each full stroke actuation of the pump.

Although a user can actuate a foam dispensing pump, or a squeeze foam dispensing package, across a broad range (for example, for a manually-actuable pump, from about 0.20 seconds per pump stroke to about 3.00 seconds per pump stroke), under typical use conditions the pump is actuated at a rate of from about 0.35 seconds to about 2.20 seconds per stroke, more preferably from about 0.50 to about 1.40 seconds per stroke. The volume of foam dispensed with each full stroke of the pump can be varied depending upon the concentration of the foamable liquid to be used by the end user, and the amount of air to be mixed with the liquid to generate the foam. Conventional foam pumps can be used in the practice of the present invention. Conventional foam pumps typically dispense a volume of foam from about 10 cm³ to about 50 cm³, more typically about 20 cm³, with each full pump stroke. Therefore, the volume rate of foam Q which is typically dispensed from a manually-actuated pump typically ranges from about 4 cm³/sec to about 140 cm³/sec, more typically from about 14 cm³/sec to about 40 cm³/sec.

(b) Foam Dispensing Nozzle

Figure 8:
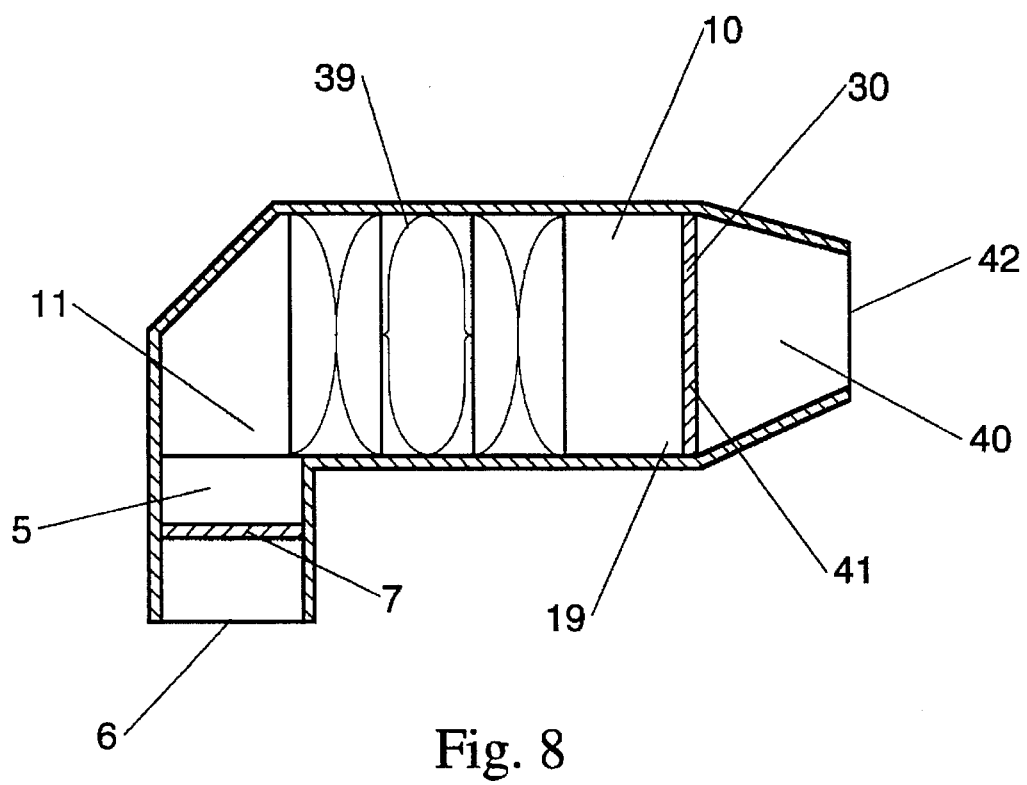
FIG. 8 shows a sectional view of a foam dispensing nozzle similar to the embodiment of FIG. 7, with a static mixer as an intermediate foam refining means.

The foam dispensing nozzle according to FIG. 8 comprises an inlet conduit 5, optional outlet conduit 40 and connecting conduit 10 in fluid communication with said manually-actuable means for receiving the intermediate foam from said means; and a foam refining means located at the discharge end of said connecting conduit 10, said foam refining means comprising a plurality of substantially uniformly-sized and evenly distributed passageways; wherein said intermediate foam passes through said passageways at a velocity, $V_2$, falling within the range of a minimum velocity, $V_{2,min}$, and a maximum velocity, $V_{2,max}$, wherein the conditions needed to cause bursting of said bubbles having a diameter larger than about $D_1$ are met.

The conduit has an inlet opening for receiving the foam from the pump means and at least one foam refining means having a plurality of substantially uniformly sized and distributed passageways extending therethrough, said foam refining means being in fluid communication with said inlet, and an outlet opening for discharging the resulting foam to the user. The conduit provides for the passage of the entire foam mixture from the inlet through to the outlet opening where it is discharged for use by the consumer. The cross-sectional shape of the conduit can be square, rectangular, oval, or any other shape that provides efficient flow of the intermediate foam from the inlet opening of the conduit to the foam refining means. The typical cross-sectional shape is rectangular having a height to width ratio of from about 1:1.5 to about 1:2. The linear distance along the centerline of the conduit from the inlet to the outlet will typically be about 5 mm to about 100 mm, more preferably from about 20 mm to about 40 mm.

The foam refining means can comprise a screen, a porous ceramic frit, or other suitable rigid or semi-rigid porous structure and material. Preferably, a screen is used because it is inexpensive, easy to handle in construction, thin and compact, and can provide openings of very small size. Hereinafter, the foam refining means will be generally referred to as refining screen. This screen can also be referred to as the final (or discharge) screen, since the foam discharged therefrom generally passes directly from the device through outlet of the conduit, as described below.

The screen used as the foam refining means of the present invention comprises a plurality of substantially uniformly sized and distributed passageways extending therethrough. Each passageway of the screen has an axis and a maximum dimension typically less than about 0.175 mm as measured perpendicular to its axis, preferably in the range of about 0.020 mm to about 0.120 mm, more preferably in the range of about 0.035 mm to about 0.080 mm, and most preferably in the range of about 0.035 mm to about 0.060 mm. FIG. 10 shows an isolated passageway formed by wires 34$v$ and 34$h$.

The percent open area of the foam refining means, typically a screen, is preferably from about 15% to about 50%, more preferably from about 20% to 40%.

Figure 4:
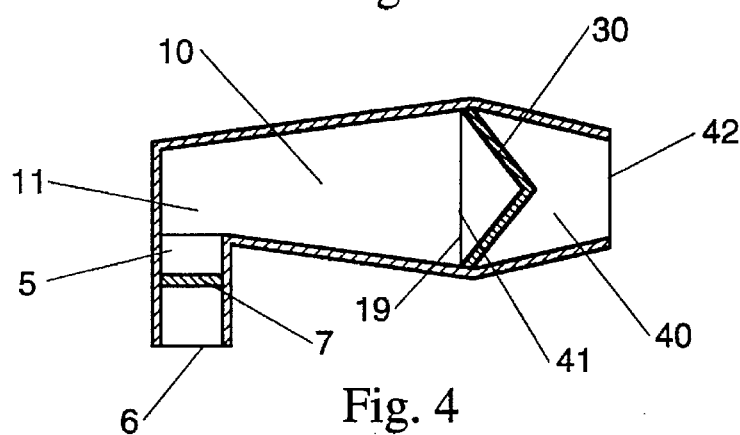
FIG. 4 shows a sectional view of another embodiment of a foam dispensing nozzle according to the present invention.

Preferably, the screen is planar and oriented in the conduit so that the axis of each of the passageways in the refining means is substantially aligned with the direction of flow through the conduit. Nevertheless, the shape of the screen can also be concave or convex with the flow of the foam mixture, or it can be a tapered cone or pyramid as shown in FIG. 4, or can be positioned as a slanted plane in the conduit, diagonally relative to the direction of fluid flow. In most applications, a planar screen positioned normal to the foam flow is preferred.

In the present invention it is preferred that the foam refining means is a screen comprising a multiplicity of substantially uniformly sized and distributed passageways located therein, each of the passageways having an axis, each of the passageways also having a maximum cross-sectional dimension D in the range of about 10% to about 40% of bubble diameter $D_1$, more preferably in the range of about 10% to about 20% of bubble diameter $D_1$, as measured perpendicular to its axis, and a length of the passageway, $L_p$, of at least about 50% of the maximum cross-sectional dimension D, as measured parallel to its axis. The screen is oriented within the conduit so that the axis of each of the passageways in the screen is generally aligned with the direction of flow through the conduit. The refining screen has a total area corresponding essentially to that of the conduit at the point where the foam refining screen is located. The refining screen is provided with a sufficient number of passageways such that the total flow area provided in the refining screen is between about 1/7 and about 1/2, more preferably between about 1/5 and about 4/10 of the cross-sectional area of the conduit, as measured at the point where the foam screen is located, whereby the ratio of the average foam velocity $V_2$ through each of the passageways in the screen to the average foam velocity $V_1$ just prior to entry into the passageways in the screen is from about 2 to about 7, more preferably from about 2.5 to about 5.0 for any volumetric flow rate Q of foam.

A suitable meshed screen is supplied by NBC Industries Co., Ltd., Tokyo, Japan, and will range from about No. 100T (D of about 0.183 mm, 52% open area) and finer; preferably from about No. 150T (D of about 0.120 mm, 46% open area) to about No. 460T (D of about 0.022 mm, 16% open area); more preferably from about No. 200S (D of about 0.082 mm, 42% open area) to about No. 355T (D of about 0.037 mm, 26% open area). The screen can also have wires in one direction which are different in type or count than the wires in the perpendicular direction. An example of such a screen is a dual-mesh screen, such as a 183 by 264 mesh screen having a 0.053 mm opening and 21% open area.

The total screen area can range from about 0.5 cm$^2$ to about 10 cm$^2$, preferably from about 1 cm$^2$ to about 3 cm$^2$, and more preferably from about 1 cm$^2$ to about 2 cm$^2$.

In yet another preferred embodiment, for the same intermediate foam and for a foam refining means having an effective passageway diameter D of from about 0.030 mm to about 0.080 mm, a high quality final foam can be made by passing said foam through the refining means at a velocity $V_2$ of about 300 cm/sec or less. As the velocity of the entering foam mixture exceeds this velocity range, the foam quality becomes poorer; that is, large bubbles can result and/or discrete streams of liquid can readily drain from the resulting foam. Preferably, a refining screen is used having a passageway diameter D from about 0.037 mm to about 0.060 mm, and a percent open area from about 26% to about 36%.

The number of passageways in the refining screen, and thus the total area of the screen, must be sufficient to produce a foam velocity $V_2$ through each of the passageways that is greater than the minimum velocity $V_{2,min}$, but not greater than the maximum velocity $V_{2,max}$, even when the volumetric flow rate of the foam through the screen is as low as about 4 cm$^3$/sec, and as high as about 140 cm$^3$/sec.

Another embodiment of the present invention which can achieve the objective of the above-defined pump foam dispenser provides for a foam refining means positioned in the conduit which is of sufficient cross-sectional area, and of sufficient open area, to enable the intermediate foam which is discharged by the foam pump to be sufficiently reduced in velocity prior to passing through the refining screen and while flowing through the passageways of the refining screen so as to achieve an improved quality foam. Such pump foam dispenser comprises an integrally-mounted foam refining nozzle as previously described.

Yet another embodiment Of the present invention further comprises a second foam refining means located in the inlet conduit of the foam dispensing nozzle. In yet another embodiment of the present invention the second foam refining means comprises a meshed screen having a plurality of substantially uniformly-sized and evenly distributed passageways.

OVER-SIZED FOAM PUMP DISCHARGE TUBE

Another embodiment of such a pump foamer dispenser comprises manually-actuable pump means which comprises an over-sized pump discharge tube, such that the volume of foam mixture exits from the pump discharge tube at a velocity much slower than that velocity from a conventional, manually-actuable foam pump, operating under the same pump actuation conditions. For a typical foam volume of 20 cm$^3$ (per one stroke) and a 0.5 second per stroke pump actuation rate (fastest typical actuation rate), the cross-sectional area of such over-sized pump discharge opening should be at least about 0.4 cm$^2$. More preferably, a cross-sectional area of about 0.8 cm$^2$ or more, usually 0.8–5 cm$^2$, is used to provide a foam mixture discharge velocity from the pump discharge tube of about 20–50 cm/sec. The foam dispensing nozzle which is attached to the over-sized pump discharge tube will generally have a conduit of the same cross-sectional area as the discharge tube, although an expanded conduit section can be used to further reduce the velocity of the foam mixture prior to entering a final screen. Likewise, the total area of the refining screen will generally have the same or larger area as that of the discharge tube; that is, from about 0.8 cm$^2$ or larger. It would not generally be desirable to increase the velocity of the foam mixture prior to passing it through the final refining screen. A refining screen as herein above defined is used to form the final foam which is dispensed to the user. Using a refining screen having a total area of 0.8 cm$^2$ or larger provides a velocity through the refining screen of less than about 200 cm/sec when pumping such foam at the typical foam volume rates of from about 12.5 cm$^3$/sec to about 40 cm$^3$/sec. Although such pump foam dispenser is particularly useful with foamable liquids having a usage viscosity of about 50 cps or more, it can also be used with foamable liquids of any viscosity to form a stable homogeneous foam.

INTERMEDIATE FOAM REFINING MEANS

As discussed above, a single refining screen is ordinarily sufficient to practice the present invention, although a second refining screen in the inlet conduit can also be used. However, one or more intermediate foam refining means located in the connecting conduit between the second foam refining means and the foam refining means located at the discharge end of the connecting conduit of the foam dispensing nozzle can be used to improve the quality of the intermediate foam entering the final refining means, primarily by reducing the number of large-diameter bubbles and by narrowing the bubble size distribution, which in turn result in an improvement of the quality of the final foam. For example, a foam produced using a coarse-mesh homogenizing screen 7 in the inlet conduit of the foam dispensing nozzle in combination with a fine-mesh refining discharge screen at the discharge end of the connecting conduit of the nozzle can generally be improved by adding either an additional intermediate screen or a static mixer between the two original screens.

The connecting conduit which houses the intermediate and discharge foam refining means can have the same cross-sectional area along the flow path of the intermediate foam (i.e., between the inlet of the connecting conduit and its outlet 19), or an expanding cross-sectional area with various rates and degrees of expansion. The total cross-sectional area of the intermediate foam refining means can range from about 0.5 cm² to about 10 cm², preferably from about 1 cm² to about 3 cm², and more preferably from about 1 cm² to about 2 cm². The intermediate foam refining means is selected from the group consisting of meshed screens, static mixers and combinations thereof. In one embodiment the intermediate foam refining means comprises a meshed screen; and in yet another embodiment the intermediate foam refining means comprises a static mixer.

Figure 7:
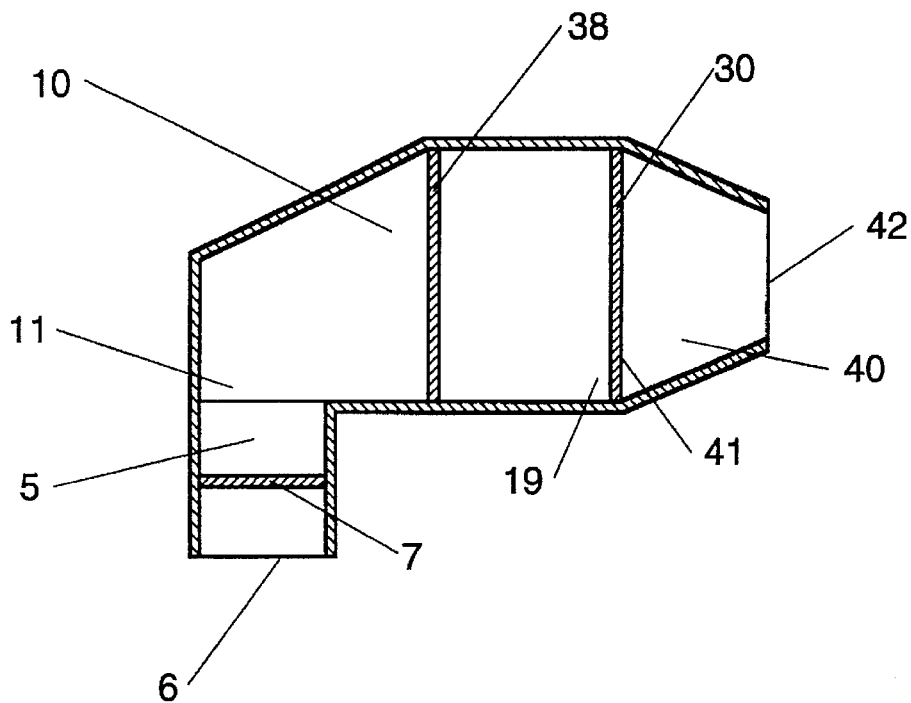
FIG. 7 shows a sectional view of a foam dispensing nozzle similar to the embodiment of FIG. 2b, said nozzle further including an intermediate foam refining means shown therein as a screen.

FIG. 7 shows an intermediate foam refining means as a screen 38 mounted in the connecting conduit 10 upstream of the final screen 30. The intermediate screen 38 can be placed at any position between the inlet of the connecting conduit 10 and the outlet 19. Intermediate screen 38 generally meets the bubble break-up conditions established for the discharge screen 30 as discussed above. A dispensing nozzle using an intermediate screen is generally capable of improving the persistence of the foam. The selection of the intermediate screen can be optimized based on the properties of the foamable liquid, the configuration of the final refining screen and the conditions discussed above. For example, a three-screen foam refining nozzle with screens having mesh sizes corresponding to 100T, 183 by 264 dual, and 355T (inlet, intermediate, and final refining screens) and using a 19 cps foamable liquid, dispenses a foam which is more persistent than that dispensed from a three-screen nozzle with screens of mesh sizes 100T, 305, and 355T. The latter foam is approximately as persistent as the foam dispensed from the same foam dispensing nozzle but without the 305 intermediate screen. The two intermediate screens have the same passageway opening D (0.053 mm); but the 305 mesh intermediate screen has 41% open area, whereas the 183 by 264 dual-mesh screen has only a 21% open area. The difference is believed attributable to whether or not the conditions for bubble break-up are achieved for each intermediate screen.

The percentage open area of the intermediate meshed screen is preferably from about 10% to about 40%, and more preferably from about 15% to about 30%. The intermediate screen has a plurality of uniformly-sized and evenly distributed passageways having a maximum dimension as measured perpendicular to its axis, preferably in the range of about 0.020 mm to about 0.120 mm, more preferably in the range of about 0.035 mm to about 0.080 mm, and most preferably in the range of about 0.035 mm to about 0.060 mm. In one embodiment of the present invention, the intermediate foam refining means comprises a meshed screen; and wherein the dimension D of the substantially uniformly-sized and evenly distributed passageways ranges from about 5% to about 20% of the number-average bubble diameter $D_1$ of the final foam. For foamable liquids having viscosity from about 20 cps to about 80 cps, the $V_{2,min}$ is preferably from about 15 cm/sec to about 30 cm/sec, and more preferably from about 20 cm/sec to about 30 cm/sec; and the $V_{2,max}$ is preferably from about 100 cm/sec to about 350 cm/sec, and more preferably from about 100 cm/sec to about 300 cm/sec.

FIG. 8 shows the intermediate refining means as static mixer 39. Static mixers, also referred to as motionless mixers, are known in the fluid mixing art and can be made of various materials and in many sizes and shapes. A preferred static mixer can have two or more helical elements, arranged in alternating left- and right-hand pitch. An example of such a static mixer is a three-element Kenics Static Mixer, having a diameter of 1.27 cm (0.5 in.) and a length of 3.81 cm (1.5 in.). Since commercially-available static mixers usually have a round cross section, it is preferred to use a connecting conduit also having a round cross section to accommodate the static mixer.

A nozzle which includes a static mixer as an intermediate foam refining means can also dispense quality foams from foamable liquids ranging in viscosity from about 20 cps to about 130 cps. The dispensed foams are more persistent that those from typical two-screen nozzles and less sensitive to actuation dynamics (i.e., liquid drainage and foam thickness data is generally more constant and does not depend on how fast or slow the user actuates the pump). The static mixer provides shear rate and residence time for bubble break-up and can also break bubbles by the mechanism of flow division. The static mixer can also homogenize the dispersion of bubbles into the continuous liquid phase. As a result the foam which emerges out of the static mixer can be expected to be homogeneous and to contain bubbles with a more uniform bubble size distribution and smaller average bubble size. The final refining screen breaks the bubbles even further.

For foamable liquids having viscosity from about 20 cps to about 80 cps, the $V_{2,min}$ is preferably from about 15 cm/sec to about 40 cm/sec, and more preferably from about 20 cm/sec to about 40 cm/sec; and the $V_{2,max}$ is preferably from about 200 cm/sec to about 400 cm/sec, and more preferably from about 200 cm/sec to about 350 cm/sec.

The more elements that a static mixer system has, the better the bubble break-up and homogenization that are achieved. However, there is a practical limit on the number of elements that can be employed. The extent to which intermediate foam refining means (e.g. screens and static mixers) are employed is determined by practical limitations such as costs, aesthetics, and physical or mechanical considerations. The physical or mechanical considerations referred to above concern the necessary force needed to actuate the foam dispenser. Specifically, placing any foam refining means in the conduit prior to the final foam refining means can increase back pressure, resulting in increased resistance to manual operation of the pump means. Therefore, the intermediate foam refining means should only be used to the extent that it does not create user-objectionable effort to pump the dispenser.

Alternate Embodiments:Squeeze Foamers and Aerosol Dispensers

In alternative embodiments, the foaming compositions of the present invention are also contemplated to be deliverable from other types of dispensers having a foam dispensing nozzle described above. Examples of alternative dispensers are conventional squeeze foamer packages which can be fitted with the foam dispensing nozzle of the present invention. Prior art squeeze foamers comprise a deformable container or reservoir for containing the liquid product to be dispensed and a foamer head, nozzle, or other foam producing means. The foamer product is produced from these squeeze foamer devices by squeezing the container with the hand to force the contained liquid product through the foamer head, nozzle, or other foam producing means. However, the conventional foamer heads, nozzles, and other foam producing means of current squeeze roamers are unable to deliver the foamable compositions of the present invention as foams having the highly desirable characteristics described herein.

Squeeze foamers suitable for use herein can be provided by fitting conventional, deformable squeeze foamer containers or reservoirs with the foam dispensing nozzles of the present invention. Conventional, squeeze foamer containers and reservoirs useful for fitting with the foam dispensing nozzles of the present invention are described in the following patents, all of which are incorporated herein by reference in their entirety: U.S. Pat. No. 3,709,437, to Wright, issued Jan. 9, 1973; U.S. Pat. No. 3,937,364, to Wright, issued Feb. 10, 1976; U.S. Pat. No. 4,022,351, to Wright, issued May 10, 1977; U.S. Pat. No. 4,147,306, to Bennett, issued Apr. 3, 1979; U.S. Pat. No. 4,184,615, to Wright, issued Jan. 22, 1980; U.S. Pat. No. 4,598,862, to Rice, issued Jul. 8, 1986; U.S. Pat. No. 4,615,467, to Grogan et al., issued Oct. 7, 1986; and French Patent No. 2,604,622, to Verhulst, published Apr. 8, 1988.

Pressurized aerosol delivery systems are also well-known in the art and generally comprise a reservoir (usually a metal canister) for containing the composition to be dispensed and the propellant (usually a gas or liquefied gas) for dispensing the composition, a dip tube, and a nozzle. Aerosol delivery systems can be prepared by fitting a canister and dip tube with a nozzle of the present invention and charging the delivery system with the composition to be delivered and a suitable propellant. The level of propellant, based on the total weight of the cleansing composition plus the propellant, is such that the propellant comprises from about 20% to about 90%, preferably from about 25% to about 80%, and more preferably from about 30% to about 50%, of the total composition. Examples of propellants useful herein include those selected from the group consisting of chlorinated, fluorinated, and chlorofluorinated lower molecular weight hydrocarbons (nonlimiting examples of which are the freons); nitrous oxide; carbon dioxide; butane; propane; and mixtures thereof.

METHOD OF MAKING IMPROVED FOAM

The present invention includes a method for producing and dispensing a high quality foam from a foamable liquid, provided that the velocity $V_2$ of the foam from said foamable liquid is within the range of $V_{2,min}$ and $V_{2,max}$ disclosed above. Therefore any foamable liquid is useful in the present invention. It is preferred however that foamable liquids have a viscosity from about 1 cps to about 300 cps, more preferably from about 20 cps to about 130 cps, and most preferably from about 50 cps to about 100 cps.

The improved method comprises the steps of:

(a) mixing a quantity of said foamable liquid with a quantity of said gas to produce an intermediate foam at a volumetric flow rate Q; said intermediate foam comprises bubbles having a number-average diameter greater than about $D_1$ and a wider bubble size distribution than the final foam; and (b) passing said intermediate foam through at least one foam refining means which comprises a plurality of substantially uniformly-sized and evenly distributed passageways; wherein said intermediate foam passes through said passageways at a velocity, $V_2$, falling within the range of a minimum velocity, $V_{2,min}$, and a maximum velocity, $V_{2,max}$, wherein the conditions needed to cause bursting of said bubbles having a diameter larger than about $D_1$ are met.

The number-average bubble diameter, $D_1$, of the foams dispensed by using the method of the present invention can range from about 0.05 mm to about 1.0 mm, more preferably from about 0.1 mm to about 0.6 mm, and most preferably from about 0.2 mm to about 0.4 mm.

Methods for Cleansing the Skin or Hair

The personal cleansing products of the present invention are useful for cleansing the skin or hair. Typically, a suitable amount of the cleansing composition is directly applied as a foam from the non-aerosol to the skin or hair to be cleansed. It is preferred to premoisten the skin or hair with water. Alternatively, a suitable amount of the cleansing composition can be applied to the skin or hair to be cleaned via intermediate application to the hands, a washcloth, a sponge, or other application device. It has been found that the compositions of the present provide their optimal cleansing performance when combined with water during the cleansing process. To complete the cleansing process, the compositions of the instant invention are thoroughly rinsed from the skin or hair with water. Suitable amounts of cleansing agent range from, but are not limited to, about 0.5 mg/cm² to about 5.0 mg/cm² of skin area or skin area underlying the hair to be cleansed.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLE I

Foam producing cleansing product.

| Ingredient | % Weight/Weight |
|---|---|
| Water | QS100 |
| Lauryldimonium Hydroxypropyl Hydrolyzed Collagen[1] | 7.14 |
| Hexylene Glycol | 6.50 |
| Decyl Polyglucose[2] | 6.00 |
| Lauryl Polyglucose[3] | 6.00 |
| Laurdimonium Hydroxypropyl Oxyethyl Cellulose[4] | 5.67 |
| Honey Extract | 5.00 |
| Glycerol | 3.00 |
| Sodium Isostearoyl Lactylate | 1.00 |
| Fragrance | 0.35 |
| DMDM Hydantoin Iodopropynyl Butylcarbonate | 0.10 |
| Tetrasodium EDTA | 0.10 |

The above ingredients are mixed together using conventional mixing techniques. The resulting foamable cleansing composition is placed in a nonaerosol dispensing device of the present invention, comprising a dual chamber pump roamer manufactured by Daiwa Can as described in Japanese Laid-Open Utility Model No1 Hei 3-7963 fitted with a foam dispensing device of the present invention essentially as shown in FIG. 1. The Daiwa Can pump roamer has a foam mixture discharge tube having a 0.6 cm inner diamer (0.28 cm²). The foam dispensing device 10 has a homogenizing screen 7 (100T mesh, about 0.193 mm opening, 52% open area) and a foam generating screen 30 (355T mesh, 26% open area, and 0.037 mm nominal opening) in the expanding conduit 10 having total area of 2.16 cm².

The resulting foam producing product is useful for application to the skin or hair for cleansing purposes and delivers a foam having a density from about 0.01 gm/cm³ to about 0.25 gm/cm³.

EXAMPLE II

Foam producing cleansing product.

| Ingredient | % Weight/Weight |
|---|---|
| Water | QS100 |
| Hexylene Glycol | 8.50 |
| Lauryldimonium Hydroxypropyl Hydrolyzed Collagen[1] | 7.14 |
| Laurdimonium Hydroxypropyl Oxyethyl Cellulose[4] | 5.67 |
| Honey Extract | 5.00 |
| Lauryl Polyglucose[2] | 4.00 |
| Decyl Polyglucose[3] | 3.00 |
| Glycerol | 3.00 |
| Urea | 3.00 |
| Glycerin (and) Water (and) Mixed Mucopolysaccharides (and) Glycogen[5] | 2.00 |
| Sorbitol (and) Sodium Lactate (and) Proline (and) Sodium PCA (and) Hydrolyzed Collagen[6] | 2.00 |
| 6-(N-acetylamino)-4-oxahexyltrimonium chloride[7] | 2.00 |
| Sodium Isostearoyl Lactylate | 1.00 |
| Fragrance | 0.23 |
| DMDM Hydantoin Iodopropynyl Butylcarbamate | 0.10 |
| Tetrasodium EDTA | 0.10 |

The above ingredients are mixed together using conventional mixing techniques. The resulting foamable cleansing composition is placed in a nonaerosol dispensing device as described in Example I.

The resulting foam producing product is useful for application to the skin or hair for cleansing purposes and delivers a foam having a density from about 0.01 gm/cm³ to about 0.25 gm/cm³.

EXAMPLE III

Foam producing cleansing product.

| Ingredient | % Weight/Weight |
|---|---|
| Water | QS100 |
| Hexylene Glycol | 9.00 |
| Lauryidimonium Hydroxypropyl Hydrolyzed Collagen[1] | 7.14 |
| Decyl Polyglucose[2] | 6.00 |
| Lauryl Polyglucose[3] | 6.00 |
| Laurdimonium Hydroxypropyl Oxyethyl Cellulose[4] | 5.67 |
| Honey Extract | 5.00 |
| Urea | 5.00 |
| Glycerol | 3.00 |
| Sodium Isostearoyl Lactylate | 1.00 |
| Lauryl Pidolate | 1.00 |
| Ammonium Cocoyl Isethionate[8] | 1.00 |
| Fragrance | 0.35 |
| DMDM Hydantoin Iodopropynyl Butylcarbamate | 0.10 |
| Tetrasodium EDTA | 0.10 |

The above ingredients are mixed together using conventional mixing techniques. The resulting foamable cleansing composition is placed in a nonaerosol dispensing device as described in Example I.

The resulting foam producing product is useful for application to the skin or hair for cleansing purposes and delivers a foam having a density from about 0.01 gm/cm³ to about 0.25 gm/cm³.

EXAMPLE IV

Foam producing cleansing product.

| Ingredient | % Weight/Weight |
|---|---|
| Water | QS100 |
| Hexylene Glycol | 7.77 |
| Lauryldimomium Hydroxypropyl Hydrolyzed Collagen[1] | 7.14 |
| Decyl Polyglucose[2] | 6.00 |
| Lauryl Polyglucose[3] | 6.00 |
| Laurydimonium Hydroxypropyl Oxyethyl Cellulose[4] | 5.67 |
| Honey Extract | 5.00 |
| Glycerol | 3.00 |
| Lauryl Pidolate | 2.00 |
| Ammonium Cocoyl Isethionate[8] | 1.00 |
| Fragrance | 0.23 |
| DMDM Hydantoin Iodopropynyl Butylcarbamate | 0.10 |
| Tetrasodium EDTA | 0.10 |

The above ingredients are mixed together using conventional mixing techniques. The resulting foamable cleansing composition is placed in a nonaerosol dispensing device as described in Example I.

The resulting foam producing product is useful for application to the skin or hair for cleansing purposes and delivers a foam having a density from about 0.01 gm/cm³ to about 0.25 gm/cm³.

EXAMPLE V

Foam producing cleansing product.

| Ingredient | % Weight/Weight |
|---|---|
| Water | QS100 |
| Decyl Polyglucose[2] | 6.00 |
| Lauryl Polyglucose[3] | 6.00 |
| Honey Extract | 5.00 |
| Protonated Polyethylenimine[9] | 3.50 |
| Glycerol | 3.00 |
| Hexylene Glycol | 2.00 |
| Fragrance | 0.23 |
| DMDM Hydantoin Iodopropynyl Butylcarbamate | 0.10 |
| Tetrasodium EDTA | 0.10 |

The above ingredients are mixed together using convention mixing techniques. The resulting foamable cleansing composition is placed in a nonaerosol dispensing device as described in Example I.

The resulting foam producing product is useful for application to the skin or hair for cleansing purposes and delivers a foam having a density from about 0.01 gm/cm³ to about 0.25 gm/cm³.

EXAMPLE VI

Foam producing cleansing product.

| Ingredient | % Weight/Weight |
|---|---|
| Water | QS100 |
| Hexylene Glycol | 7.77 |
| Decyl Polyglucose[2] | 6.00 |
| Lauryl Polyglucose[3] | 6.00 |
| Laurdimonium Hydroxypropyl | 5.67 |

-continued

| Ingredient | % Weight/Weight |
|---|---|
| Oxyethyl Cellulose[4] | |
| Honey Extract | 5.00 |
| Lauryldimonium Hydroxypropyl Hydrolyzed Collagen[1] | 3.50 |
| Glycerol | 3.00 |
| Hydrolyzed Casein[10] | 3.00 |
| Lauryl Pidolate | 2.00 |
| Ammonium Cocoyl Isethionate[8] | 1.00 |
| Fragrance | 0.23 |
| DMDM Hydantoin Iodopropynyl Butylcarbamate | 0.10 |
| Tetrasodiium EDTA | 0.10 |

The above ingredients are mixed together using convention mixing techniques. The resulting foamable cleansing composition is placed in a nonaerosol dispensing device as described in Example I.

The resulting foam producing product is useful for application to the skin or hair for cleansing purposes and delivers a foam having a density from about 0.01 gm/cm$^3$ to about 0.25 gm/cm$^3$.

EXAMPLE VII

Alternatively, the compositions described in Examples I-VI above are prepared containing from about 0.1% to about 2% of one or more active materials selected from among the following: salicylic acid, erthromycin, benzoyl peroxide, dihydroxyacetone, ibuprofen, hydrocortisone, lidocaine, triclosan, zinc pyrithione, selenium sulfide, chlorhexidene, 2-ethylhexyl 4-N,N-dimethyl-p-aminobenzoate, 2-ethylhexyl p-methoxycinnamate, octocrylene, octyl salicylate, homomenthyl salicylate, p-aminobenzoic acid, oxybenzone, 2-phenylbenzimidazole-5-sulfonic acid, DEA p-methoxycinnamate, 4,4'-methoxy-t-butyldibenzoylmethane, 4-isopropyl dibenzoylmethane, 3-(4-methylbenzylidene) camphor, 3-benzylidene camphor, and mixtures thereof.

EXAMPLE VIII

Antibacterial Foaming Cleansing Product with Triclosan

| Ingredient | % Weight/Weight |
|---|---|
| Water | QS100 |
| Lauryidimonium Hydoxypropyl Hydrolyzed Collagen | 7.14 |
| Alkyl Polyglucose | 6.00 |
| Lauryl Polyglucose[3] | 6.00 |
| Laurdimonium Hydroxypropyl Oxyethyl Cellulose[4] | 5.67 |
| Honey Extract | 5.00 |
| Glycerin | 3.00 |
| Hexylene Glycol | 2.77 |
| Ammonium Cocoyl Isethionate[8] | 1.00 |
| Triclosan | 0.25 |
| Fragrance | 0.23 |
| Tetrasodium EDTA | 0.10 |
| DMDM Hydantoin Iodopropynyl Butylcarbamate | 0.10 |

The above ingredients are mixed together using convention mixing techniques. The resulting foamable cleansing composition is placed in a nonaerosol dispensing device as described in Example I.

The resulting foam producing product is useful for application to the skin or hair for cleansing purposes and delivers a foam having a density from about 0.01 gm/cm$^3$ to about 0.25 gm/cm$^3$.

EXAMPLE IX

Foaming cleansing Product with Salicylic Acid

| Ingredient | % Weight/Weight |
|---|---|
| Water | QS100 |
| Cocamidopropyl PG-Dimonium Chloride Phosphate | 10.00 |
| Polyvinyl Pyrollidone* | 20.00 |
| Laurdimonium Hydroxypropyl Oxyethyl Cellulose[4] | 3.50 |
| Salicylic Acid | 2.00 |
| Hexylene Glycol | 2.00 |
| Glycerin | 2.00 |
| Tetrasodium EDTA | 0.10 |
| DMDM Hydantoin/Idopropynyl Butylcarbamate | 0.10 |
| Menthol | 0.05 |

*Alternatively, this formula is prepared replacing the 20% Polyvinyl pyrollidone with 10% Polyvinyl pyrollidone and 1% Protonated polyethylenimine[9]

The above ingredients are mixed together using convention mixing techniques. The resulting foamable cleansing composition is placed in a nonaerosol dispensing device as described in Example I.

The resulting foam producing product is useful for application to the skin or hair for cleansing purposes and delivers a foam having a density from about 0.01 gm/cm$^3$ to about 0.25 gm/cm$^3$.

EXAMPLE X

Nonaresol Foam Dispenser

A) Pump Foam Dispenser I

A dual chamber pump foam dispenser manufactured by Daiwa Can as described in Japanese Laid-Open Utility Model No. Hei 3-7963 is mounted onto a suitable container, and is fitted with a foam dispensing nozzle of the present invention essentially as shown in FIG. 1. The Daiwa Can foam pump has a foam mixture discharge tube having a 0.6 cm inner diameter (area of 0.28 cm$^2$). The foam pump discharges a foam mixture of liquid and air having a volume of 20 cm$^3$ for each full stroke of the pump. The foam dispensing nozzle 1 of the present invention has an inlet opening of about 0.5 cm$^2$, a homogenizing screen 7 (100T mesh size, 0.183 mm opening size, and 52% open area) having a total area of 0.16 cm$^2$ positioned in the inlet conduit 5, and a foam refining screen 30 (355T mesh size, 0.037 mm opening size, and 26% open area) in the expanded conduit 10 having a total area of 1.0 cm$^2$. The foamable liquid Composition of Example I, having a viscosity of about 50 cps to about 100 cps (at 25° C.), is placed into the container and the pump and dispensing nozzle assembly is attached. When the pump is actuated at a rate of about 0.5–1.4 seconds per stroke, a thick, stable and homogeneous foam is made, having a negligible amount of larger bubbles, and is very uniform.

B) Pump Foam Dispenser II

A dual chamber pump foam dispenser manufactured by Daiwa Can as described in Japanese Laid-Open Utility Model No. Hei 3-7963 is mounted onto a suitable container, and is fitted with a foam dispensing nozzle of the present invention essentially as shown in FIG. 8. The Daiwa Can foam pump has a foam mixture discharge tube having a 0.6 cm inner diameter (area of 0.28 cm$^2$). The foam pump discharges a foam mixture of liquid and air having a volume of 20 cm$^3$ for each full stroke of the pump. The foam dispensing nozzle of the present invention has an inlet conduit of about 0.5 cm², a homogenizing screen 7 (100T mesh size, 0.183 mm opening size, and 52% open area) having a total area of 0.16 cm² positioned in the inlet conduit 5, a static mixer 39 of Kenics type with 3 helical elements of alternating left- and right-hand pitch located in the connecting conduit 10, wherein the diameter of the static mixer is 1.27 cm (0.5 in.), and a foam refining screen 30 (183 by 264 dual-mesh size, 0.053 mm opening size, and 21% open area) at the discharge end of the connecting conduit 10 having a total area of 1.27 cm². The foamable liquid Composition of Example I, having a viscosity of about 50 cps to about 100 (at 25° C.), is placed into the container and the pump and dispensing nozzle assembly is attached. When the pump is actuated at a rate of about 0.45–2.00 seconds per stroke, a thick, stable and homogeneous foam is made, having a negligible amount of larger bubbles, and is very uniform. Furthermore, when the pump is actuated at a rate of about 0.45–2.00 seconds per stroke, the dispensed foam exhibits liquid drainage characteristics which are independent of the actuation dynamics.

C) Prior Art Dispenser

In comparison, the same dual chamber foam pump of Examples XA and XB is fitted with a conventional foam dispensing nozzle which has an inlet opening of about 0.5 cm², a homogenizing screen 7 (100T mesh size, 0.183 mm opening size, and 52% open area) having a total area of 0.16 cm² positioned in the inlet opening 5, and a 0.34 cm², substantially-rectangular discharge conduit that has a second foam refining screen therein. The screen is a 200S mesh screen (0.082 mm opening size and 42% open area) having a total area of 0.25 cm². The foamable liquid Composition of Example I, having a viscosity of about 50 cps to about 100 (at 25° C.), is placed into the container and the pump and dispensing nozzle assembly is attached. The pump is actuated in the same manner described above in the invention example. The foam generated has a significant amount of larger bubbles and is non-uniform and runny, and the operation of the pump requires more actuation pressure than the invention examples.

What is claimed is:

1. A foam producing cleansing product comprising:

(A) a foamable cleansing liquid composition comprising
(i) from about 0.1% to about 20% of a surfactant selected from the group consisting of amphoteric surfactants, nonionic surfactants, and mixtures thereof,
(ii) from about 0.1% to about 10% of a water soluble cationic or nonionic polymer,
(iii) from about 0.1% to about 25% of a humectant,
(iv) from about 0.05% to about 10% of an emollient, and
(v) from about 35% to about 99.65% water,
wherein said liquid composition has a viscosity of from about 1 cps to about 300 cps; and (B) a foam dispenser for dispensing a final foam from an incoming intermediate foam, said dispenser comprising a reservoir to contain said liquid composition, a manually-actuated means for generating a volume of a mixture of said liquid composition and a gas, and a foam dispensing nozzle sealably attached in fluid communication with said manually-actuated means wherein the improvement comprises a nozzle comprising:
(i) an inlet conduit for receiving an intermediate foam consisting of a mixture of a liquid composition and a gas at a volumetric flow rate sufficiently high that it will produce an average incoming intermediate foam velocity which is too great to permit effective bubble bursting to put said foam in a final foam as said foam passes through at least one downstream foam refining means having a plurality of passageways therethrough; and
(ii) a velocity decreasing means placing said inlet conduit in fluid communication with a foam refining means, wherein said velocity decreasing means lowers the average velocity of said intermediate foam so when said foam passes through said foam refining means it is at a velocity no greater than 300 cm/sec.

2. A product according to claim 1 wherein said composition has a viscosity of from about 20 cps to about 130 cps.

3. A product according to claim 1 wherein said composition has a viscosity of from about 50 cps to about 100 cps.

4. A product according to claim 3 wherein said foam has a density of from about 0.05 gms/cm³ to about 0.15 gms/cm³.

5. A product according to claim 3, wherein said foam has a density of from about 0.075 gms/cm³ to about 0.125 gms/cm³.

6. A product according to claim 5 comprising from about 2.0% to about 6.0% of said water soluble polymer.

7. A product according to claim 6 wherein said water soluble polymer is selected from the group consisting of lauryldimmonium hydroxypropyl oxyethyl cellulose, laurdimonium hydroxyethyl cellulose, steardimonium hydroxyethyl cellullose, cocodimonium hydroxyethyl cellulose, lauryldimoniumu hydroxypropyl hydrolyzed collagen, lauryldimmonium hydroxypropyl hydrolyzed keratin, lauryldimmonium hydroxypropyl hydrolyzed keratin, lauryldimmonium hydroxypropyl hydrolyzed silk, lauryldimmonium hydroxypropyl hydrolyzed soy protein, protonated polyethylenimine, hydrolzyed casein, hydrolyzed collagen, hydrolyzed vegetable protein, polyvinylpyrrolidone, and mixtures thereof.

8. A product according to claim 6 wherein said water soluble polymer is selected from the group consisting of laurdimmonium hydroxypropyl oxyethyl cellulose, lauryldimonium hydroxypropyl hydrolyzed collagen, hydrolzyed casein, and mixtures thereof.

9. A product according to claim 7 wherein said surfactant is selected from the group consisting of lauryl polyglucoside, decyl polyglucoside, oleyl betaine, cocamidopropyl betaine, cocamidopropyl hydroxysultaine, sodium lauryl sarcosinate, coamdiopropyl PG-dimonium chloride phosphate, and mixtures thereof.

10. A product according to claim 9 wherein said humectant is selected from the group consisting of glycerin, urea, honey extract, 1,2-butylene glycol, 1,2-hexylene glycol, propoxylated glycerol and mixtures thereof.

11. A product according to claim 9 wherein said emollient is selected from the group consisting of sodium isostearyl lactylate, lauryl pidolate, sorbitan stearate, panthenyl triacetate, and mixtures thereof.

12. A product according to claim 9 which further comprises an active ingredient selected from the group consisting of anti-acne actives, sunscreen actives, anti-dandruff actives, artificial tanning actives, nonsteroidal antiinflammatory actives, antipruritic actives, topical anesthetic actives, antimicrobial actives, and mixtures thereof.

13. A product according to claim 9 which further comprises an active ingredient selected from the group consisting of salicylic acid, erythromycin, benzoyl peroxide, dihydroxyacetone, ibuprofen, hydrocortisone, lidocaine, triclosan, zin pyrithione, selenium sulfide, chlorhexidene, 2-ethylhexyl 4-N,N-dimethyl-p-aminobenzoate, 2-ethylhexyl p-methoxycinnamate, octocrylene, octyl salicylate, homomenthyl salicylate, p-aminobenzoic acid, oxybenzone, 2-phenylbenzimidazole-5-sulfonic acid, DEA p-methoxycinnamate, 4,4'-methoxy-t-butyldibenzoylmethane, 4-isopropyl dibenzoylmethane, 3-(4-methylbenzylidene) camphor, 3-benzylidene camphor, zincoxide, titianium dioxide and mixtures thereof.

14. A product according to claim 1 which further comprises from about 0.1% to about 2.5% of an anionic surfactant.

15. A product according to claim 9 which further comprises from about 0.1% to about 2.5% of an anionic surfactant.

16. A product according to claim 15 wherein said anionic surfactant is selected from the group consisting ammonium cocoyl isethionate, sodium cocoyl isethionate, sodium lauroyl isethionate, sodium stearoyl isethionate, and mixtures thereof.

17. A product according to claim 1 wherein said foam refining means comprises a meshed screen having a plurality of substantially uniformly-sized, and evenly distributed passageways having a maximum dimension less than about 0.175 mm as measured perpendicular to its axis.

18. A product according to claim 17 wherein said passageways of said screen have a dimension from about 0.020 mm to about 0.120 mm.

19. A product according to claim 18 wherein the total area of the refining screen is from about 0.5 cm$^2$ to about 10 cm$^2$ and the percentage open area is from about 15% to about 50%.

20. A product according to claim 17 wherein said passageways of said screen have a dimension from about 0.035 mm to about 0.080 mm.

21. A product according to claim 18 wherein the total area of the refining screen is from about 1 cm$^2$ to about 2 cm$^2$ and the percentage open area is from about 20% to about 40%.

22. A product according to claim 1 wherein said velocity decreasing means comprises a volume expanding means.

23. A product according to claim 22 wherein the volume expanding means is an expanded conduit having a cross-sectional area at its outlet at least larger than a cross sectional area of its inlet.

24. A product according to claim 23 wherein said ratio of cross-sectional areas of the outlet to inlet is from about 2:1 to about 8:1.

25. A product according to claim 24 wherein said expanded conduit has a rectangular cross sectional shape having a height to width ratio from about 1:1.5 to about 1:2.

26. A foam producing cleansing product comprising:
(A) a foamable cleansing liquid composition comprising
   (i) from about 0.1% to about 20% of a surfactant selected from the group consisting of amphoteric surfactants, nonionic surfactants, and mixtures thereof,
   (ii) from about 0.1% to about 10% of a water soluble cationic or nonionic polymer,
   (iii) from about 0.1% to about 25% of a humectant,
   (iv) from about 0.05% to about 10% of an emollient, and
   (v) from about 35% to about 99.65% water,
wherein said liquid composition has a viscosity of from about 1 cps to about 300 cps; and (B) a manually-actuable foam dispenser for producing and dispensing a high quality final foam from a foamable liquid and a gas, said foam being comprised of bubbles having a number-average diameter of about $D_1$, said dispenser comprising:
   (i) a manually-actuable means for mixing a quantity of said foamable liquid with a quantity of said gas to produce an intermediate foam which comprises bubbles having a number-average diameter greater than about $D_1$ and a wider bubble size distribution than the final foam, at a volumetric flow rate Q which is dependent upon the speed of actuation of said manually-actuable means by the user; and
   (ii) a foam dispensing nozzle comprising a conduit in fluid communication with said manually-actuable means for receiving the intermediate foam from said manually-actuable means; and at least one foam refining means located in said conduit, said foam refining means comprising a plurality of substantially uniformly-sized and evenly distributed passageways; wherein said intermediate foam passes through said passageways at a velocity, $V_2$, failing within the range of a minimum velocity, $V_{2,min}$, and a maximum velocity, $V_{2,max}$, wherein the conditions needed to cause bursting of said bubbles having a diameter larger than about $D_1$ are met.

27. A product according to claim 26 wherein said foam refining means is a meshed screen comprising a plurality of substantially uniformly-sized and evenly distributed passageways; each of the passageways having an axis; and each of the passageways also having a maximum cross-sectional dimension D in the range of about 10% to about 20% of the number-average bubble diameter $D_1$ of the final foam, as measured perpendicular to its axis.

28. A product according to claim 27 further comprising a second foam refining means located in said inlet conduit of the said foam dispensing nozzle.

29. A product according to claim 28 wherein said second foam refining means comprises a meshed screen having a plurality of substantially uniformly-sized and evenly distributed passageways.

30. A product according to claim 28 further comprising an intermediate foam refining means located in said conduit between said second foam refining means and said foam refining means located at the discharge end of said connecting conduit of the said foam dispensing nozzle.

31. A product according to claim 30 wherein said intermediate foam refining means is selected from the group consisting of meshed screens, static mixers and combinations thereof.

32. A product according to claim 31 wherein said intermediate foam refining means comprises a meshed screen; and wherein the dimension D of the substantially uniformly-sized and evenly distributed passageways ranges from about 5% to about 20% of the number-average bubble diameter $D_1$ of the final foam.

33. A product according to claim 30 wherein said intermediate foam refining means comprises a static mixer.

34. The product according to claim 31 wherein the percentage open area of said intermediate meshed screen is from about 15% to about 30%.

35. The product according to claim 26 wherein said foam dispenser is a pump foam dispenser.

* * * * *

UNITED STATES PATENT AND TRADEMARK OFFICE
CERTIFICATE OF CORRECTION

PATENT NO : 5,635,469

DATED : June 3, 1997

INVENTOR(S) : Timothy J Fowler et al

It is certified that error appears in the above-identified patent and that said Letters Patent is hereby corrected as shown below At column 4, line 56 "et at " should read --et al --

At column 4, line 57 "et at " should read --et al --

At column 5, line 39 "fatty adds" should read --fatty acids--

At column 6, line 1 "$C_7$-$C_{15}$ alkyl" should read --$C_7$-$C_{19}$ alkyl--

At column 11, line 15 "triols" should read --triols--

At column 11, line 17 "urea, honey" should read --urea, honey--

At column 11, line 66 "et at " should read --et al --

At column 12, line 3 " hydroxy" should read --hydroxy--

At column 13, line 58 "off Typical" should read --off  Typical--

At column 14, line 13 "thereof Preferred" should read --thereof  Preferred--

At column 14, lines 45-46 "provide, more" should read --provide more--

At column 14, line 64 "erthromycin" should read --erythromycin--

At column 15, lines 22-23 "See i Federal Registerl" should read --See Federal Register--

At column 15, line 56 "dimethylarninobenzoic" should read --dimethylaminobenzoic--

At column 16, line 16 "4,4-methoxy" should read --4,4'-methoxy--

At column 16, line 25 "4,4-methoxy" should read --4,4'-methoxy--

UNITED STATES PATENT AND TRADEMARK OFFICE
CERTIFICATE OF CORRECTION

PATENT NO : 5,635,469  
DATED : June 3, 1997  
INVENTOR(S) : Timothy J Fowler et al It is certified that error appears in the above-identified patent and that said Letters Patent is hereby corrected as shown below At column 16, line 50 "fleurbiprofen" should read --flurbiprofen--
At column 17, line 25 "tolnafiate" should read --tolnaftate--
At column 18, line 40 "mount" should read --amount--
At column 20, line 18 "I C Bellinger" should read --J C Bellinger--
At column 29, line 66 "Of" should read --of--
At column 32, line 62 "roamers" should read --foamers--
At column 34, line 46 "Butylcarbonate" should read --Butylcarbamate--
At column 34, line 53 "roamer" should read --foamer--
At column 34, line 56 "roamer" should read --foamer--
At column 35, line 45 "Lauryidimonium" should read --Lauryldimonium--
At column 35, line 55 "lodopropynyl" should read --Iodopropynyl--
At column 36, line 8 "Lauryldimomium" should read --Lauryldimonium--
At column 36, line 17 "lodopropynyl" should read --Iodopropynyl--
At column 37, line 14 "Tetrasodnum" should read --Tetrasodium--
At column 37, line 28 "erthromycin" should read --erythromycin--
At column 37, line 46 "Lauryidimonium" should read --Lauryldimonium--

UNITED STATES PATENT AND TRADEMARK OFFICE
CERTIFICATE OF CORRECTION

PATENT NO : 5,635,469

DATED : June 3, 1997

INVENTOR(S) : Timothy J Fowler et al

It is certified that error appears in the above-identified patent and that said Letters Patent is hereby corrected as shown below At column 39, line 41 insert the footnotes --[1] Available as an approximately 35% aqueous solution under the tradename Lamequat L from Henkel Corp

[2] Available as an approximately 50% aqueous solution under the tradename APG 325 from Henkel Corp

[3] Available as an approximately 50% aqueous solution under the tradename APG 625 from Henkel Corp

[4] Available as an approximately 20% aqueous solution under the tradename Crodacel QL Special from Croda Corp

[5] Available under the tradename Dermosaccharides HC from Laboratories Serobiologique

[6] Available under the tradename Prodew 100 from Ajinomoto Corp

[7] Available as an approximately 50% aqueous solution under the Quamectant AM-50 from Brooks Industries

[8] Available as an approximately 30% aqueous solution under the tradename Jordapon ACI-30 from PPG Mazer

[9] Available as an approximately 50% aqueous solution under the tradename Polymin P from BASF

[10] Available as an approximately 20-40% aqueous solution under the tradename Milk Q from Seiwa Kasei Co --

At column 40, line 21 "3, wherein" should read --3 wherein--

At column 42, line 21 "failing" should read --falling--

Signed and Sealed this

Third Day of February, 1998

BRUCE LEHMAN

Attest:

Attesting Officer

Commissioner of Patents and Trademarks